United States Patent [19]
Sadek et al.

[11] Patent Number: 5,146,730
[45] Date of Patent: Sep. 15, 1992

[54] FILM-ENROBED UNITARY-CORE MEDICAMENT AND THE LIKE

[75] Inventors: Hani Sadek, Calabasas; Gregory L. Dietel, Moorpark, both of Calif.

[73] Assignee: Banner Gelatin Products Corp., Chatsworth, Calif.

[21] Appl. No.: 410,134

[22] Filed: Sep. 20, 1989

[51] Int. Cl.$^5$ .............................................. B65B 47/00
[52] U.S. Cl. ...................................... 53/454; 53/546; 53/553; 53/900
[58] Field of Search ................. 53/900, 454, 453, 560, 53/559, 553, 554, 546

[56] References Cited

U.S. PATENT DOCUMENTS

| | | | |
|---|---|---|---|
| 2,219,578 | 10/1940 | Pittenger | 53/560 |
| 2,296,294 | 9/1942 | Scherer | 18/21 |
| 2,323,581 | 7/1943 | Weckesser | 53/560 |
| 2,367,802 | 1/1945 | Scherer | 53/560 |
| 2,387,747 | 10/1945 | Cowley | 53/560 |
| 2,503,518 | 4/1950 | Slaughter | 53/560 |
| 2,513,852 | 7/1950 | Donofrio | 53/560 |
| 2,608,405 | 8/1952 | Salfisberg | 53/560 |
| 2,663,128 | 12/1953 | Stirn et al. | 53/5 |
| 2,697,317 | 12/1954 | Stirn et al. | 53/89.5 |
| 2,775,080 | 12/1956 | Stirn et al. | 53/26 |
| 2,836,291 | 5/1958 | Stroop | 206/56 |
| 3,228,789 | 1/1966 | Glassman | 117/118 |
| 4,281,763 | 8/1981 | Pace | 206/530 |
| 4,567,714 | 4/1986 | Chasman | 53/454 |
| 4,820,524 | 4/1989 | Berta | 424/474 |

FOREIGN PATENT DOCUMENTS

| | | | |
|---|---|---|---|
| 535783 | 1/1957 | Canada | 53/454 |
| 2141094 | 10/1981 | United Kingdom | 53/454 |

OTHER PUBLICATIONS

"Packaging Technology", vol. 17, No. 2, Mar./Apr. 1987, pp. 3,4,7 and 16.

*Primary Examiner*—Thurman K. Page
*Assistant Examiner*—Raj Bawa
*Attorney, Agent, or Firm*—Christie, Parker & Hale

[57] ABSTRACT

A medicine tablet is described as a new article of manufacture. The table is enrobed in a gelatin coating formed by application of respective layers of elastic gelatin film to opposite sides of the tablet. The applied gelatin layers conform tightly to the tablet surface, bond securely to the tablet, and are sealed together in essentially edge-to-edge manner at a seal line which extends around the tablet at a desired place on the tablet. The gelatin layers can be colored differently from the tablet and differently from each other. A range of formulations are described for film which can be peelable from a tablet or other product core, and for films which bond to the core. A presently preferred formulation for producing tablets having a bonded tamper-evident coating comprises a water-based gelatin preparation having about 45% gelatin and about 9% plasticizer (glycerin and/or sorbitol) by weight.

Method and apparatus for producing such new products are also described. Product cores can be dispensed on a self-timed basis into essentially simultaneous contact with two enrobing films which are supported on locally recessed coacting rotary dies. The cores contact the films adjacent a nip between the dies at places on the films which overlie die recesses which are oversize relative to the cores. The films deform around each core and are sealed by the dies to each other before the dies coact to cut the enrobed cores from the films. A core feeding mechanism can include an alignent device which causes the cores to have a desired orientation as they are handled by the dies.

54 Claims, 12 Drawing Sheets

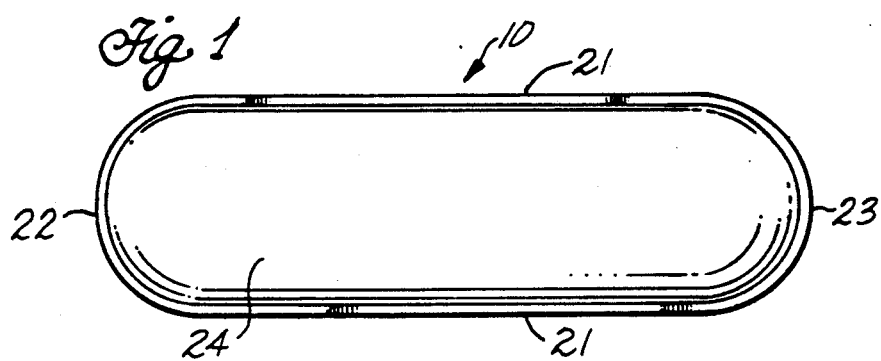
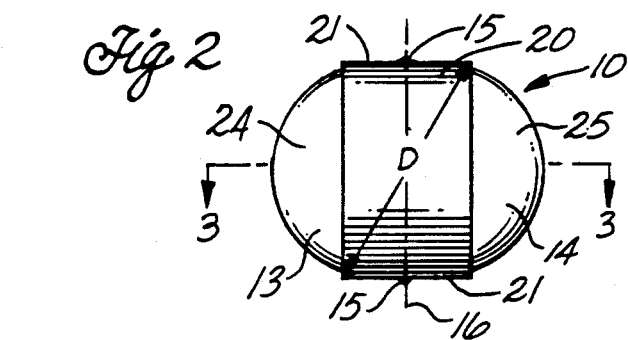
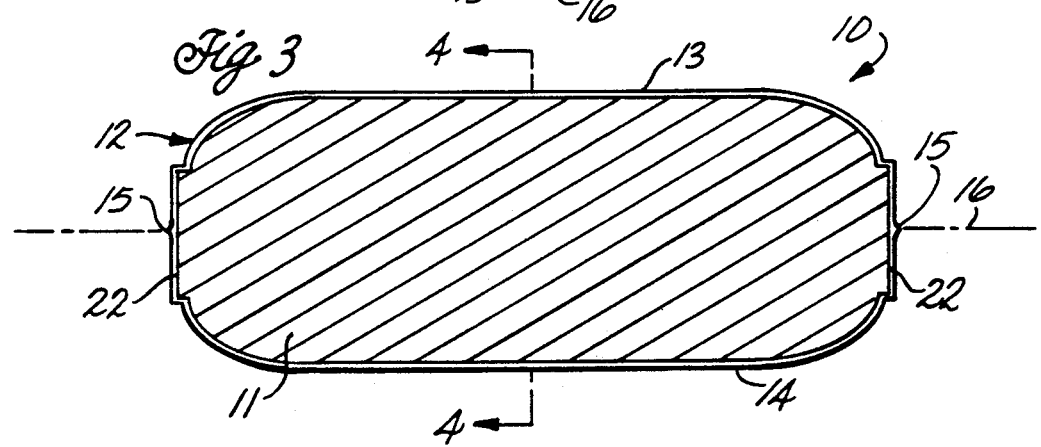
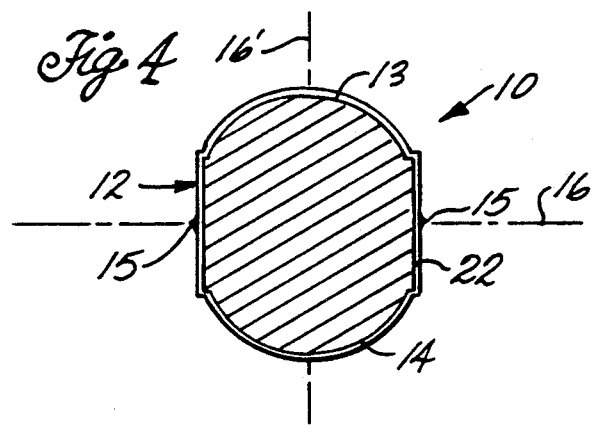

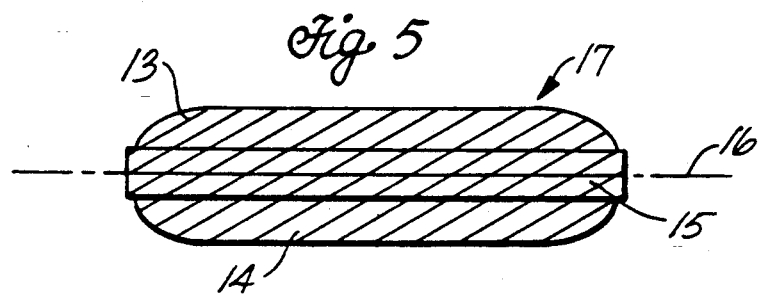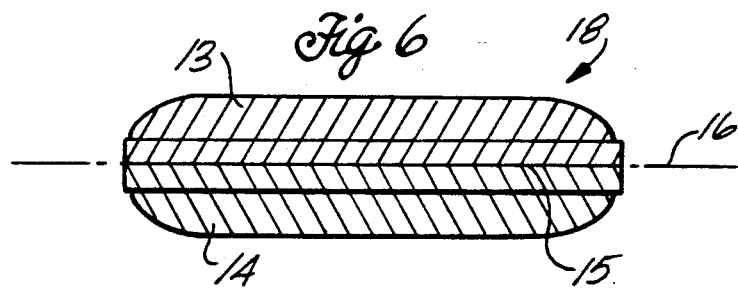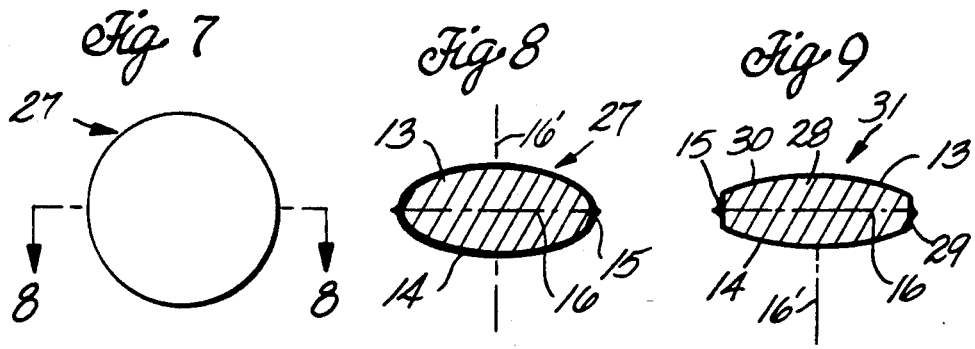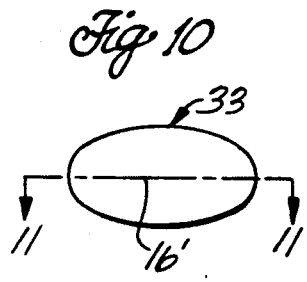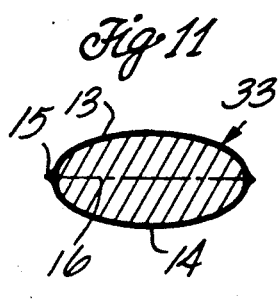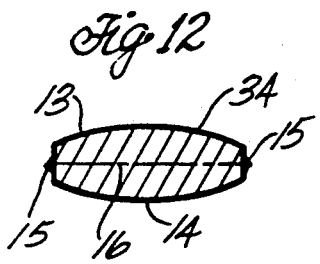

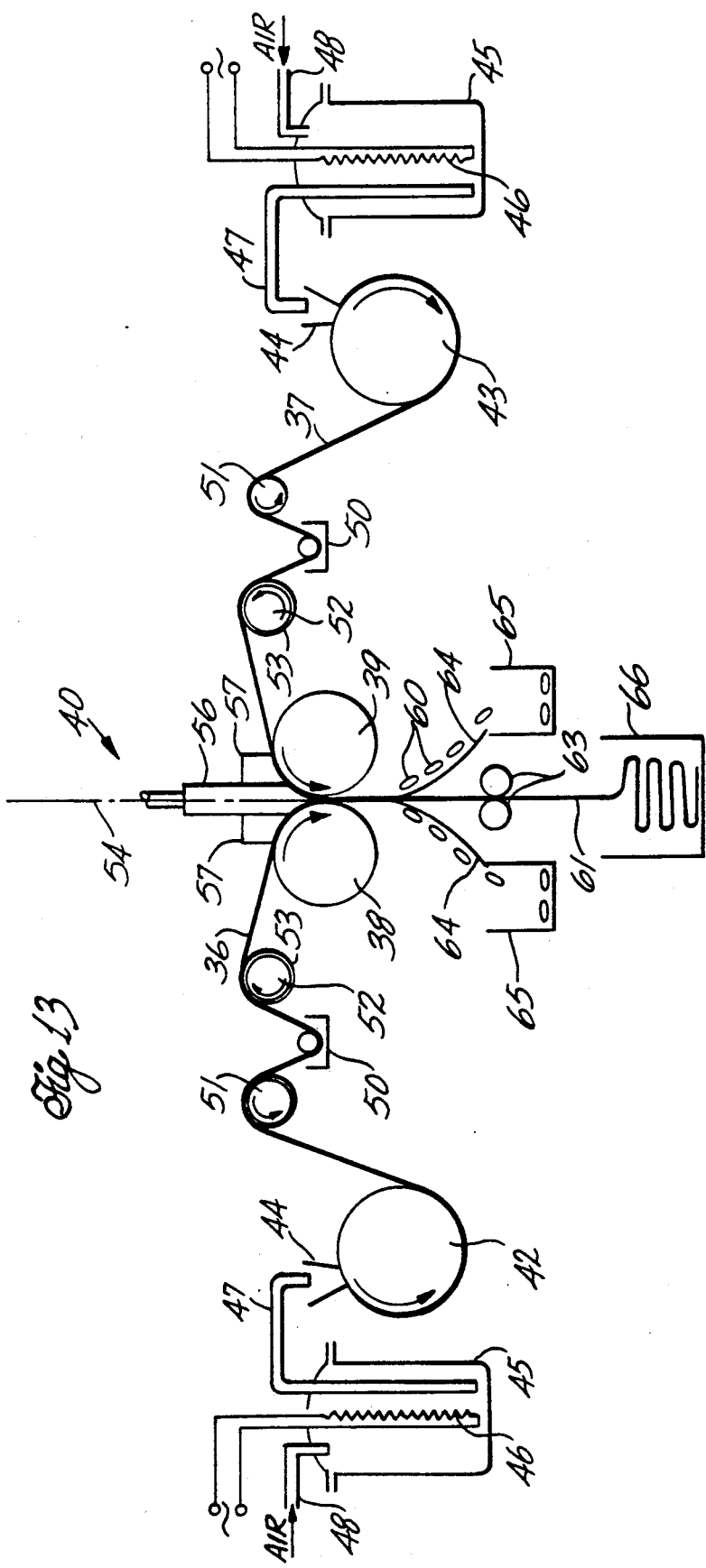

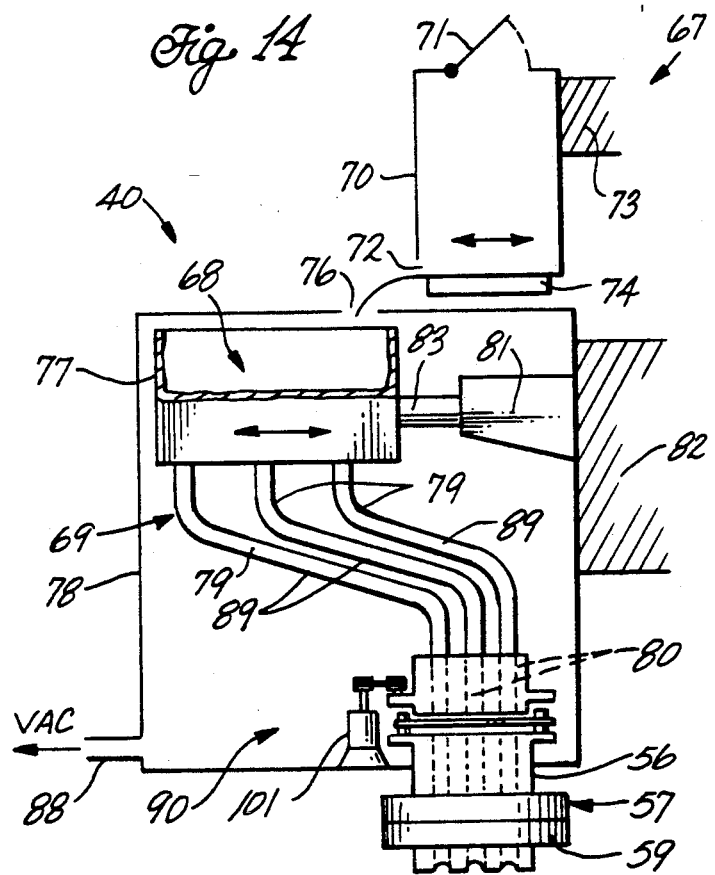

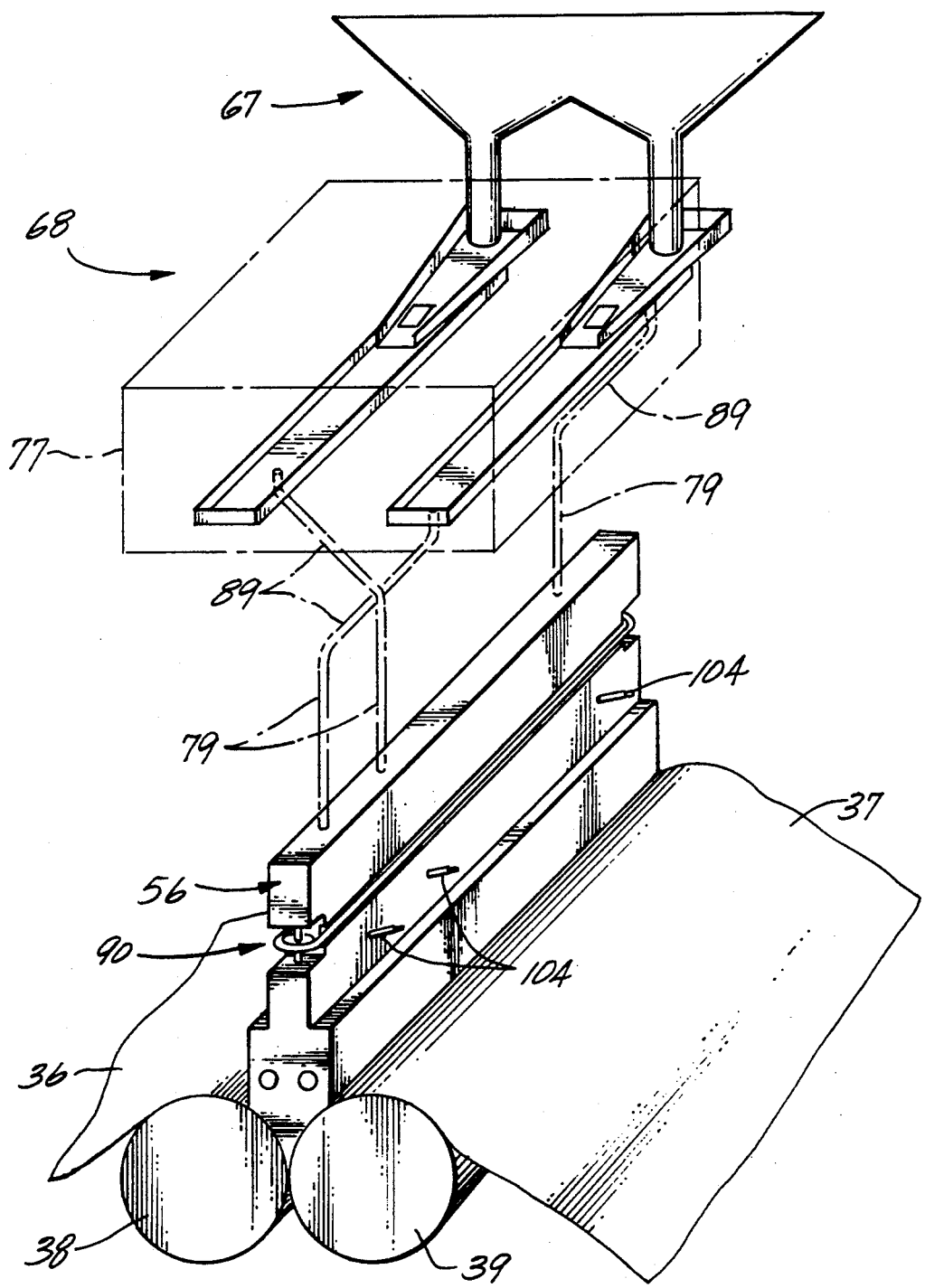

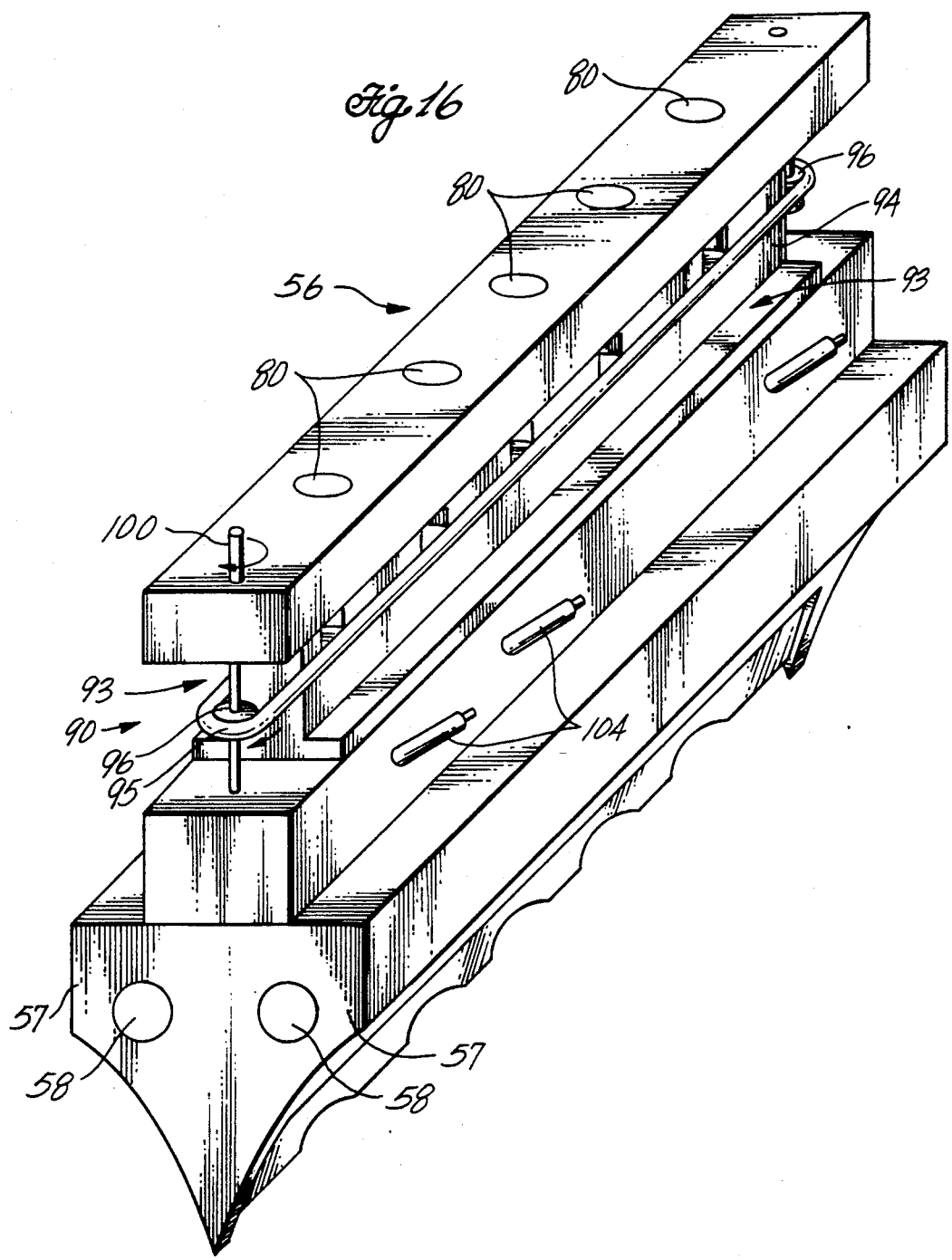

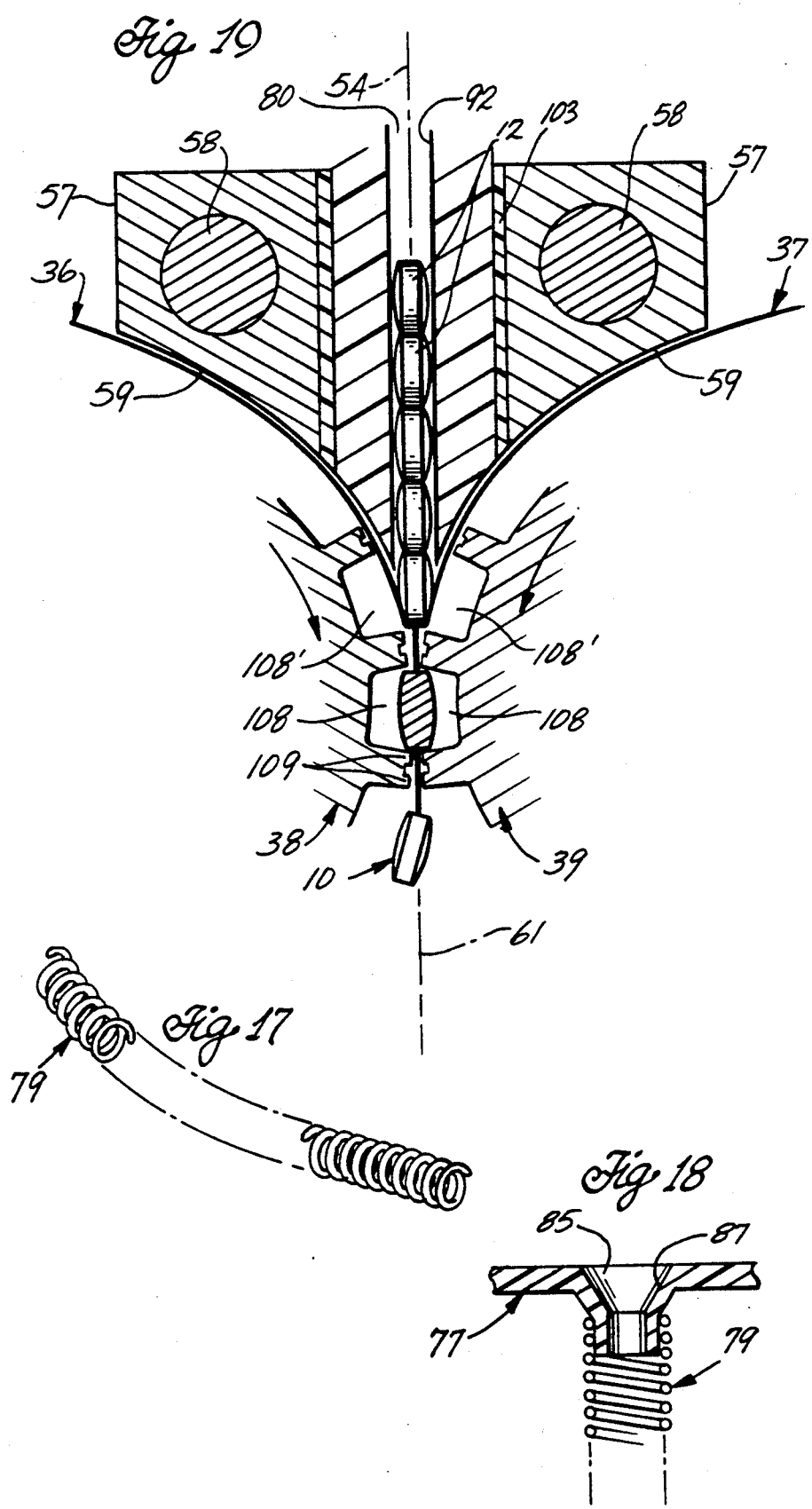

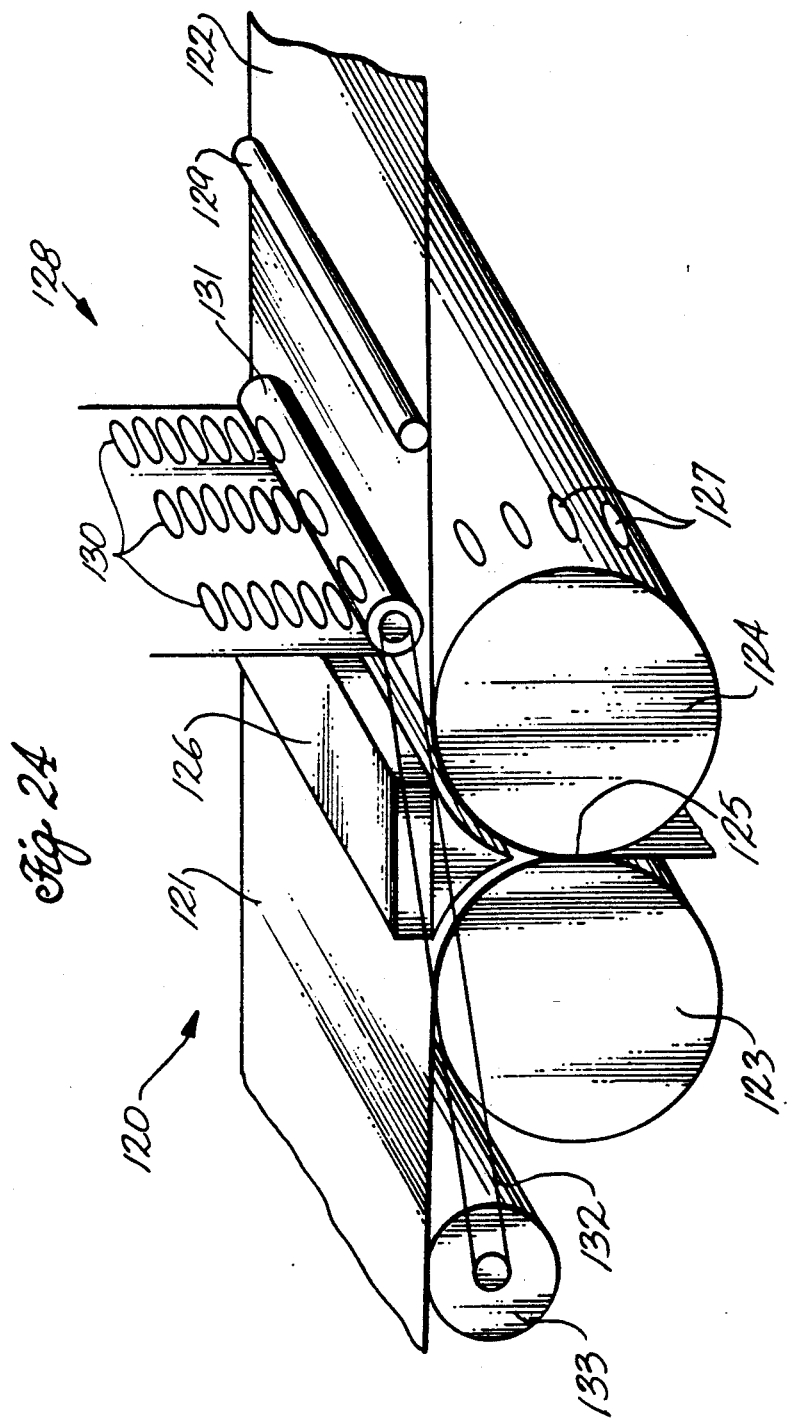

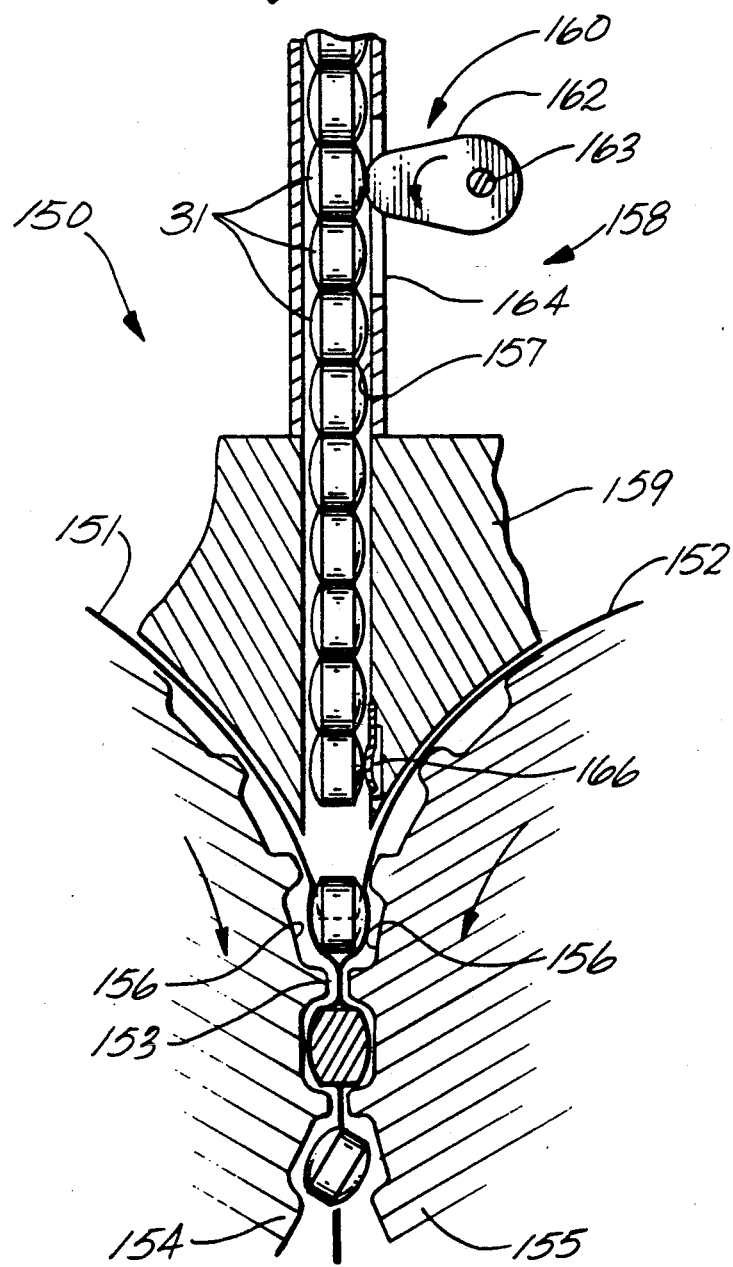

FILM-ENROBED UNITARY-CORE MEDICAMENT AND THE LIKE

FIELD OF THE INVENTION

This invention pertains to film-enrobed unitary-core products such as medicine tablets, to films and film compositions for making such products, and to methods and equipment for manufacturing such products. More specifically, within a presently preferred area of that field, the invention pertains to medicines and the like comprising cores of one-piece tablet nature in various geometrical forms which are enrobed in preferably digestible or erodable films applied to the cores separately from formation of the cores; the invention also pertains to gelatin-based and other films for enrobing such cores, to methods for enrobing such cores with such films, and to equipment for performing such methods to produce such products.

BACKGROUND OF THE INVENTION

The pharmaceutical, vitamin and related industries have long used various ways to present their products to users in swallowable oral dosage forms, other than purely as liquids, so that persons using such products can use them conveniently and comfortably. Broadly, orally used non-liquid medicines and the like are provided in two general forms. One form is a tablet in which the dosage unit is a solid, hard swallowable shape comprised of the desired active ingredients compressed and formed with suitable binders into an integral article. Tablets, in their broadest sense, are available in many shapes and sizes. The other common solid dosage is a capsule in which the active ingredients occur in a flowable state (powder, liquid, paste or the like) and are encased in a digestible shell of a suitable shape and form which is swallowable. Variations exist within and between these two general forms. Thus, it is known to coat, as by dipping or spraying, tablet-type dosage units with gelatin or other materials to make them more palatable, easier to swallow, less prone to powder or to flake when handled in bottles, colored for eye appeal or identifiability, and longer lasting before active ingredients degrade, among other reasons. Capsule forms of such products occur as soft gelatin capsules, which commonly are of spherical or oblate spherical shape, and as hard gelatin capsules which commonly are of elongated round-ended cylindrical form and which are made in two pieces for assembly, with or without sealing, around the flowable fill material containing the desired active ingredients.

The portion of U.S. Pat. No. 4,820,524 entitled "Background of the Invention" (which portion is incorporated herein by reference) presents a comprehensive and good review of hard gelatin encapsulated medicines and the like, and of certain forms of solid medicaments having spray-applied or dip-applied gelatin coatings. That review is presented as an introduction to the invention of that patent which is a caplet (a tablet shaped to resemble a hard gelatin capsule) dipped first at one end and then at its other end in liquid gelatin to form, upon drying of the gelatin, a gelatin coating fully enclosing the preformed, base solid caplet. The text of that review notes that, because of the problem of tampering which had been experienced with hard gelatin capsule products, many manufacturers of such products withdrew them from the market in favor of other forms of active-ingredient presentment, notably caplets. The withdrawal of hard gelatin encapsulated products from the market left those manufacturers with idle machines for making hard gelatin capsules, a situation which U.S. Pat. No. 4,820,524 addressed by its descriptions of how such machinery could be modified to produce an at least twice-dipped, gelatin-coated caplet form of medicine. The resulting final product can be colored uniformly, or it can be colored differently at its opposite ends by differently tinting the gelatin baths into which each of the opposite ends of the caplet preform is dipped at least once. A number of advantages of such products over hollow hard gelatin capsules and over pan-coated tablets are noted in U.S. Pat. No. 4,820,524 at column 11, lines 19 et seq.

In its detailed description, namely, at column 10, lines 47 et seq., U.S. Pat. No. 4,820,524 notes that the dipping of preformed caplets into wet gelatin baths can have disadvantageous effects, and that precoating of the caplet with a sealant, such as a moisture barrier, can be useful.

While the procedures described in U.S. Pat. No. 4,820,524 for producing at least twice-dipped, gelatin-coated caplets are relatively simple, the machinery required for high-volume implementation of those procedures is quite complex, extensive and expensive. Also, those procedures and that machinery are not well suited for handling solid medicament preforms in shapes other than caplet shape.

In the context of soft gelatin capsules and the procedures and equipment for their manufacture, there have occurred descriptions of ways to produce approximations of gelatin coated tablets. The usual soft encapsulated gelatin product is one in which a flowable fill material (powder, paste or liquid) containing the desired active ingredient is pumped under pressure into place where two films of soft elastic gelatin are brought together between rotating or reciprocating dies with which the films are in contact. The dies have cavities formed in their surfaces. The pumping of fill material between the plastic gelatin films is carefully timed in synchronism with die movement so that a metered amount of fill is discharged between the films to cause the films to bulge into adjacent opposed die cavities. The films come together around a controlled amount of fill as the dies continue to move and the films are then sealed together by applying pressure and/or heat at the dies which then coact to cut the films at the seal. The then fully-enclosed-by-gelatin fill dosage quantity separates from the films as a discrete article. That article may then be washed to remove film lubricants (such as mineral oil) and then dried to provide the finished product which is suitably packaged for sale.

U.S. Pat. Nos. 2,663,128 (1953), 2,697,317 (1954), and 2,775,080 (1956), all issued to F. E. Stirin and A. S. Taylor as assignors to American Cyanamid Company, describe complex procedures and equipment in which a suitable active ingredient powder is formed into a soft pellet. The pellet is transferred by a vacuum holding mechanism into registry with and dispensed into a cup-like depression formed by vacuum in a plastic gelatin film. The cup-like depression can also contain a liquid. Thereafter, the film which defines the loaded depression is moved into contact with a second gelatin film which is sealed across the depression. The loaded and sealed depression is cut from the adhered pair of films, and the product then self-adjusts its shape to a desired tablet, sphere, or capsule-like shape, after which it is processed similarly to a conventional soft encapsulated gelatin capsule.

More recently *(Packaging Technology,* March/April 1987, Vol 17, No. 2, pp. 4, 7 and 16), equipment and methods for encasing a pair of half-dose softly-compacted tablet-like preforms between converging soft elastic gelatin films have been described. So far as is known, such equipment was not successfully built and operated.

These earlier descriptions of adaptations of soft elastic gelatin encapsulated tablet-like products in the Stirin et al patents and the *Packaging Technology* article teach that the tablet is formed as a soft preform and that such formation occurs in the same machinery which encloses the preform between two soft gelatin films. Such teaching is inconsistent with the actual development and present state of the industry which produces soft elastic gelatin capsules. That industry is based upon substantial investments of capital, time and human experience and is comprised of firms which are essentially packagers of products of others. Those firms either receive the flowable active-ingredient fill materials produced by others such as pharmaceutical manufacturers or vitamin compounders, or they formulate the fill material under the control of and in compliance with the specifications of others. They then pump that flowable material into place between two soft gelatin films in machines which they own and operate under controlled conditions. They then deliver the finished capsules in bulk back to their customers who package and market the capsules under their own names. Present reality is that tablet manufacture is one industry and soft elastic gelatin capsule manufacture is a separate and distinct industry. Members of one industry are reluctant to invest the capital and other resources necessary to acquire the equipment and skills, and also the risks and responsibilities, present in the other industry; they prefer, for sound reasons, to keep the industries separate and to trade between the industries in the manner described. The teachings of the Stirin et al patents and the *Packaging Technology* article call for a blending of those separate industries. That blending has not occurred and likely will not occur for the reasons noted. A need exists for gelatin enrobed tablets which are free of the problems noted in U.S. Pat. No. 4,820,524 occasioned by the necessarily high temperature and high moisture content of gelatin baths into which caplets can be dipped. A need exists for technology useful to enable members of the soft elastic gelatin capsule industry to apply their resources and talents to the manufacture of gelatin enrobed tablets without requiring that industry to, in effect, blend with the tablet manufacturing industry. A need exists for improved procedures and equipment which are compatible with the existing investments and skills in the soft elastic gelatin capsule industry, and which will enable members of that industry to receive from the tablet industry tablets of various sizes and shapes, to individually package those tablets in soft films, and to deliver such packaged tablets back to the tablet industry for market packaging and distribution. A need exists for a way for the soft elastic gelatin capsule industry to support and service the tablet manufacturing industry in providing improved film enrobed tablets without disturbing the existing working relationships between those industries. This invention addresses those needs and, in so doing, provides an improved tablet product.

Previously published documents considered in the development and patenting of this invention include the following documents:

U.S. Pat. Nos. 2,296,294, 2,663,128, 2,697,317, 2,775,080, 2,836,291, 3,228,789, 4,281,763, and 4,820,524, and *Packaging Technology,* Vol. 17, No. 2, March/April 1987, pages 4, 7 and 16.

SUMMARY OF THE INVENTION

This invention provides an improved dosage form, among other kinds of products, in which a solid tablet preform or core is fully enrobed in soft elastic film material, such as a gelatin film, in a relatively dry state and at relatively low temperature. Formation of the tablet can occur at times and at places segregated from the time and place where the tablet is film-enrobed. The substantially dry and low temperature nature of the tablet enrobing process is important to the integrity and life of the active ingredients in the tablet. The film enrobing the tablet can tightly bond to the tablet so that, especially when the film is distinctively colored, the enrobed tablet is tamper-evident. The enrobing films can be colored to produce monocolored or bicolored enrobed tablets. The enrobed tablets can be further processed to have enteric coatings so that when swallowed, the tablets pass through the stomach and dissolve in the intestines; the film enrobing the tablet can protect the tablet from undesirable reactions with constituents of the enteric or other coatings applied over the film. The enrobed tablet can be so enrobed as to have significantly more strength and resistance to breakage when handled or subsequently processed than the unenrobed tablet.

This invention also provides improved film compositions for use in enrobing tablets and other things for various purposes. The compositions include a soft elastic gelatin film which provides a securely bonded enrobement around a solid tablet, thereby providing a tablet having enhanced tamper-evident properties.

The invention also provides improved methods and equipment which are readily adaptable to and implementable with related procedures and machinery in place in the soft elastic gelatin capsule manufacturing industry to produce the improved tablets described above. Implementation and practice of these aspects of the invention does not require large scale replacement, reworking or remanufacture of existing soft elastic gelation encapsulation machinery or procedures, and can be accomplished rapidly and with economic efficiency and without undesired disruption of established business practices and relationships.

Generally speaking, according to one aspect of the invention, this invention provides a new article of manufacture comprised of a unitary article preform of selected shape and size which is fully enrobed between two layers of applied elastic film material of selected thickness and composition, which layers substantially conform to the contours of the preform and which are sealed to each other along a single line encircling the preform and lying substantially in a common plane. The film layers, when applied to the preform, exhibit substantially low water activity and have an elastic plastic character.

A presently preferred such article of manufacture is one in which the preform is a tablet of selected size and shape containing a desired amount of at least one selected active ingredient. The film material applied in tablet-enrobing manner to the tablet is a gelatin-base film so formulated that, as applied to and sealed around the tablet, it conforms tightly to the tablet contours and bonds securely to the tablet surfaces, is colored differently from the tablet, and dries to a hard state. The resulting product is stronger than the preform itself and provides a readily visible indication of efforts to remove the enrobing film from the tablet, whereby the enrobed tablet is tamper-evident.

According to another aspect of the invention, this invention provides an improved soft elastic gelatin composition useful to form the enrobing film for the presently preferred article of manufacture. The composition as initially formulated comprises 45% by weight gelatin, 9% by weight glycerol as a plasticizer, and the balance consisting essentially of water and such colorants as may be useful. The gelatin has a bloom value in the range of from 150 to 180.

According to still another aspect of the invention, this invention provides a method for film enrobing of unitary preforms such as medicinal tablets of desired composition, shape and size. The method includes the steps of providing a pair of films, moving the films, heating the films, dispensing article preforms to the films, contacting the films peripherally around the preforms from opposite sides of the preforms, sealing the contacted films to each other around the preforms, and separating the preforms as so enrobed by the films from the films. The films are provided to have selected thickness and composition. When heated to a predetermined temperature within a selected range of temperatures, the films are elastic, plastic and self-adhering to each other. The films have obverse surfaces which come together during performance of the contacting step. The films are moved at essentially equal velocities along selected paths which pass through a place of coaction of a pair of coacting dies where the obverse surfaces of the films are brought into contact with each other. The dies have cooperating working surfaces which are configured to form between them, on coaction of the dies, at least one cavity which is sized and shaped for loosely receiving therein a single article preform. Heating of the films is performed on the obverse surface of at least one of the films, which surface is heated to the predetermined temperature. Heating is performed at a location along the paths proximate to the place of die coaction. In preform dispensing, one preform for each cavity formed between the coacting dies is dispensed individually into contact with the obverse surface of at least one of the films at a location which corresponds to the location of a cavity. The dispensed preform moves with the film to the place of die coaction. Contacting of the films is performed at the place of die coaction. The films are contacted with each other around the preforms to cause each preform to be enrobed between the films and by the films. As separated from the films after the sealing step is performed, each single preform as sealed between layers of the film material comprises an article of manufacture produced by the method.

According to yet another aspect of the invention, the invention provides apparatus for film enrobing a series of essentially identical separate article preforms of selected size and shape. The apparatus comprises a pair of matching dies which have coacting working surfaces which are configured for defining between the dies, upon movement of the working surfaces into coacting relation at a selected place, at least one cavity of sufficient size and shape to receive loosely therein a single one of the article preforms. Film moving means are provided and are operable for moving two elastic and cosealable films of selected thickness and composition along respective paths which converge at the place of coaction between the die working surfaces with the films disposed in overlying relation to the respective cavity defining features of the die surfaces. Means cooperate with the film paths for creating in the films moving therealong to the place of die coaction predetermined conditions of plasticity and axial tension in the films as disposed in overlying relation to the die working surfaces. Preform dispensing means are located proximate the place of die coaction and are operable for dispensing preforms individually to at least one of the films in a selected orientation of the dispensed preforms relative to the dies at respective film locations which correspond to the die cavities. The dispensed preforms move with the at least one film to the place of die coaction for enrobing engagement at that place between the films within the die cavities. Drive means move the dies into and out of coacting relation at the desired place along the file paths. The dies are formed to cause them, when moving into the coacting relation, to apply the films to the preforms from opposite sides of the preforms, to cut the film layers applied to the preforms from the remainder of the films, and to seal the applied film layers to each other in essentially edge-to-edge relation about the preforms. The apparatus also includes means for separating the converged films from film enrobed preforms.

According to a still further aspect of the invention, the invention provides a die which is useful with a similar cooperating die for enrobing between a pair of films of soft elastic material of selected thickness individual ones of a plurality of essentially identical medicine tablets and the like. The tablets have specified overall geometry and size, and have rounded edge configurations. The tablets are supplied toward a substantially linear place of coaction of the die with its cooperating die along a path which is substantially normal to the place of die coaction and which is disposed substantially symmetrically between the dies. The die comprises a drum-like article which is rotatable in a selected direction about an axis. The die has a substantially circularly cylindrical outer working surface in which are formed at regularly spaced intervals along at least one line circumferentially about the working surface a plurality of essentially identical recesses. Each recess has an opening shaped geometrically similarly to the geometry of one of the tablets and each recess is dimensioned to be oversize relative to the tablet. Each recess is bounded by a rim which conforms to the shape of the recess opening. The rim of each recess at least at a portion of the recess on the corresponding line of recesses towards the direction of die rotation is relieved a selected amount away from the recess.

BRIEF DESCRIPTION OF THE DRAWINGS

The above mentioned and other features of this invention are more fully set forth in the following detailed description of presently preferred and other embodiments of the various aspects of this invention, which description is presented with reference to the accompanying drawings in which:

FIG. 1 is a top plan view of a gelatin film enrobed tablet of caplet configuration which is the presently preferred product produced by practice of this invention;

FIG. 2 is an end elevation view of the gelatin film enrobed caplet shown in FIG. 1;

FIG. 3 is a cross-section view taken along line 3—3 in FIG. 2;

FIG. 4 is a cross-section view taken along line 4—4 in FIG. 3;

FIG. 5 is a side elevation view of a gelatin film enrobed caplet in which the enrobing film is uniformly colored over the entire extent of the product;

FIG. 6 is a side elevation view of a gelatin film enrobed caplet in which the enrobing film located on one side of a longitudinal plane of symmetry of the caplet is of one color, and the film lying on the other side of that plane of symmetry is of a different color;

FIG. 7 is a top plan view of a film enrobed round, but not spherical, tablet provided as another product of this invention;

FIG. 8 is a cross-section view taken along line 8—8 in FIG. 7;

FIG. 9 is a cross-section elevation view of another round tablet which is another product of this invention and which has, in top plan view, an appearance similar to that shown in FIG. 7;

FIG. 10 is a top plan view of an oval film enrobed tablet which is another product of this invention;

FIG. 11 is a cross-section view taken along line 11—11 in FIG. 10;

FIG. 12 is a cross-section elevation view of another oval tablet which, in top plan view, has a configuration like that shown in FIG. 10;

FIG. 13 is a simplified, partially schematic depiction of presently preferred apparatus useful to provide the presently preferred and other film enrobed tablets shown in FIGS. 1-12; FIG. 13 also illustrates certain of the presently preferred procedural aspects of this invention;

FIG. 14 is a simplified, partially schematic, elevation view of tablet feeding mechanisms useful with the apparatus and procedure shown in FIG. 13;

FIG. 15 is a simplified fragmentary perspective view of a tablet feeding mechanism for a production form of the apparatus and process depicted in FIG. 13;

FIG. 16 is an enlarged perspective view of a portion of the feeding mechanism shown in FIG. 15, namely, the final stage of the tablet feeding mechanism which is intimately associated with the die rolls which are shown in simplified form in FIG. 15;

FIG. 17 is a fragmentary elevation view of the presently preferred tablet guide tubes provided between the intermediate and final tablet feed mechanisms shown in simplified form in FIGS. 14 and 15;

FIG. 18 is a fragmentary, enlarged cross-sectional elevation view of the connection of the upper end of the tablet guide tube shown in FIG. 17 to the intermediate stage tablet feeder mechanism in the presently preferred production apparatus according to this invention;

FIG. 19 is a fragmentary, somewhat simplified, cross-sectional elevation view of the final stage tablet feeding mechanism and die rolls in the presently preferred apparatus according to this invention for manufacturing the presently preferred film-enrobed caplet-style tablets shown in FIGS. 1-6;

FIG. 24 is a simplified, fragmentary, perspective view of another tablet feeding and die arrangement useful in the practice of this invention;

FIG. 26 is an enlarged, fragmentary, cross-section elevation view of another form of final stage tablet feeding mechanism useful in the practice of this invention.

DESCRIPTION OF THE ILLUSTRATED EMBODIMENTS

Figure 20:
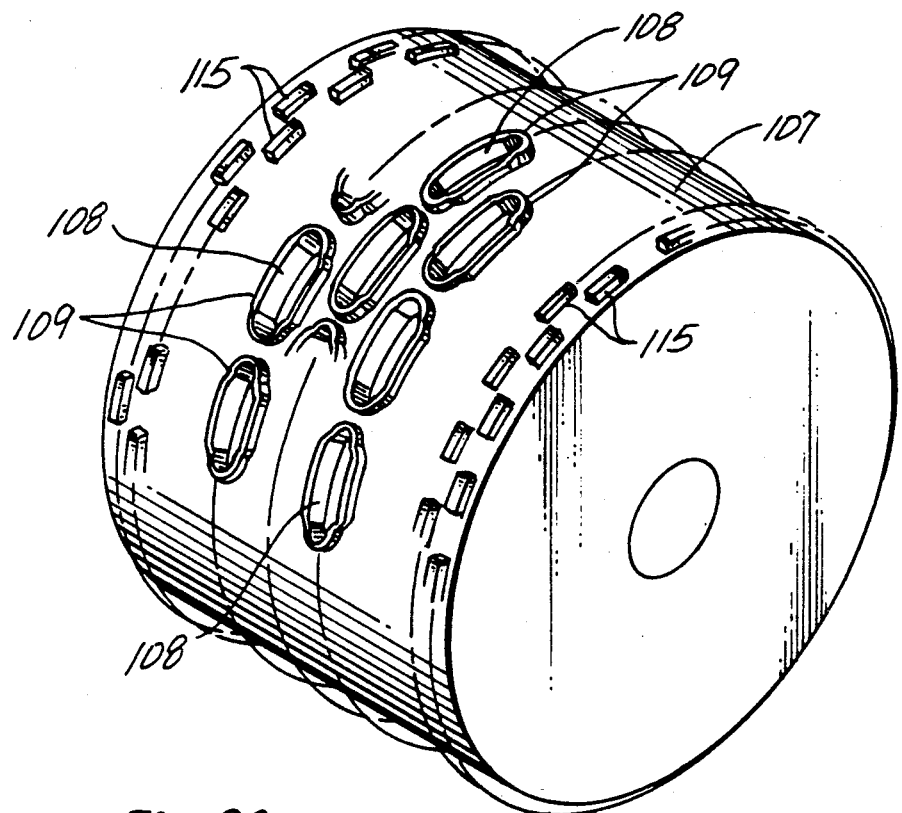
FIG. 20 is a perspective view of one of the die rolls shown in FIG. 19.

In broad terms, this invention concerns the coating of tablets, other solid dosage forms, and a variety of solids by enrobement with films of gelatin or other sealable polymers by an enrobement process which uses coacting die techniques in which the tablets or other articles to be enrobed are introduced individually between two sealable films positioned between opposing matching dies configured to cause the films to stretch and deform around each introduced article so that the films move into contact with each other, are sealed to each other and, as sealed, are severed from the film webs to provide individual film-enrobed end products. The particular product which formed the focus of the development of this invention is a tablet of caplet configuration enrobed between applied gelatin films which adhere to the solid tablet core of the product to produce a non-peelable, tamper-evident and potentially tamper-resistant gelatin coated caplet-type medicine tablet. It was found, in developing this invention, that the handling and introduction of caplet-type tablets directly to the nip between cooperating rotary die rolls, between soft elastic gelatin films wrapped on the rolls, presented one of the more difficult applications of the technology described in detail below. The invention is described below with particular reference to this presently preferred difficult production situation. The invention is also described with reference to the presently preferred equipment, procedures, and film formulations developed for producing film enrobed caplets reliably, efficiently, and at high production rates.

The hermetically-sealed applied-film coating around the tablet or other solid core of the enrobed product can be treated after production for controlled release or enteric release. Due to the continuous nature of the applied-film coating, individual coated units provide an assurance of consistent product performance.

In the following description, unless the usage context indicates otherwise, the term "tablet" is used in its broad sense to mean a solid, hard, unitary pellet containing one or more active ingredients, which pellet is of such size as to be administered by an intended user and is of desired geometry; the term includes such things having caplet configuration, which things are often referred to simply as "caplets".

FIGS. 1 through 4 are top plan and end elevation views and cross-sectional view of the presently preferred product 10 according to this invention. The product is a gelatin film enrobed caplet. The product has a core 11 and a hard gelatin coating 12 which fully encloses the core. The coating conforms tightly to the contours of the core and is adhere tightly to the surfaces of the core over the entire exterior surface extent of the core. Coating 12 is defined by layers 13 and 14 of soft elastic gelatin film which are applied to opposite sides of the core and which are sealed together, in an essentially edge-to-edge manner, along a seal line 15 which encircles the core. Seal line 15 preferably is substantially coincident with a longitudinal plane of symmetry 16 of the core. After being applied to and sealed together around the core, layers 13 and 14 dry to a hard glass-like state in which the coating is securely bonded to the core. The gelatin used to form layers 13 and 14 is formulated to produce such a finished coating.

Preferably, applied gelatin layers 13 and 14 are colored differently from the color of core 11 itself. If both applied coating layers are of the same color, the resulting product is a monocolored gelatin film enrobed caplet 17 shown in FIG. 5. On the other hand, if applied gelatin layers 13 and 14 have different colors, the resulting product is a bicolored gelatin film enrobed caplet 18 as shown i FIG. 6.

Gelatin layers 13 and 14 which together enrobe the caplet core of product 10 are provided as portions of two soft elastic gelatin films which, as cast in the machinery described below and presented to the core for enrobement of the core, have a thickness in the range of from 0.005 inches to 0.045 inches. If equipment of different definition from that described below is used, films of lesser or substantially greater thickness can be handled. As applied to the caplet core and as dried thereon, the layers 13 and 14 are of somewhat smaller thickness in product 10.

Caplet core 11 is preferably manufactured to the desired size, shape, and composition at a facility segregated from the facility where gelatin film enrobement of the caplet occurs. Caplets generally are of geometrically similar configuration and are of elongate, round-ended configuration in plan view (see FIG. 1) and have a cylindrical peripheral surface 20 which has an oblong cross-sectional configuration. Surface 20 extends along the opposite sides 21 and around the opposite ends 22 and 23 of the caplet. The distance between the parallel sides 21 of the caplet is its width, and the distance between the extremities of ends 22 and 23 is the length of the caplet. The height of the caplet is the dimension of the caplet perpendicular to its width and length. As shown in FIG. 2, the caplet has curved top and bottom surfaces 24 and 25, respectively. A caplet has three orthogonally oriented planes of symmetry. The major plane 16 of symmetry of the caplet lies parallel to the width and length of the caplet midway between the top and bottom extremities of the caplet, midway of the height of cylindrical caplet peripheral surface 20. A second caplet longitudinal plane of symmetry 16' lies parallel to the length of the caplet and perpendicular to plane 16 centrally of the width of the caplet. Plane 16 may correspond to the parting plane of the dies used to form the caplet. As shown in FIG. 2 which is an end view of caplet core 11 turned on its side, a caplet has a diagonal dimension D.

While gelatin enrobed medicinal caplets constitute the presently preferred product according to this invention, the utility and operability of the invention has been demonstrated with tablet cores of other configurations. Other exemplary products according to this invention include a round planform film coated tablet 27 shown in FIG. 10 which can have either an oval or elliptical cross-section as shown in FIG. 8 or the cross-sectional configuration shown in FIG. 9 in which the round core 28 has a circularly cylindrical peripheral surface 29 and substantially identical curved top and bottom surfaces 30. As shown in FIGS. 8 and 9, products 27 or 31 (FIG. 9) have an applied film coating completely around their exterior surfaces, which coatings are defined by cooperating top and bottom layers 13 and 14 of applied film which are connected together at a seam line 15 which extends circumferentially of the product at a plane of symmetry 16 which encompasses the greatest cross-sectional area of the product core. As noted below, in other forms of the product, the seam line can be located at other places on the product core.

Similarly, as shown in FIGS. 10 through 12, a film enrobed product 33 or 34 according to this invention can have an oval configuration when viewed from the top, i.e., plan view (see FIG. 10) and either a lengthwise cross-sectional configuration (product 33) which is the same as that shown in FIG. 8 for product 27 (see FIG. 11) or a lengthwise cross-sectional configuration (product 34) which is the same as that shown in FIG. 9 for product 31.

FIGS. 8, 9, and 10 show that the enrobed tablets there illustrated have other planes of symmetry 16' which are perpendicular to the major planes of symmetry 16 and are either disposed diametrically (FIGS. 7-9) or longitudinally (FIGS. 10-12) of the tablets. As will become apparent from the following description of the manufacturing equipment provided by this invention, film enrobed tablets can be produced with seam lines disposed in symmetry planes 16' of the caplet (FIGS. 1-6), round (FIGS. 7-9) and oblong or oval (FIGS. 10-12) tablets if such seam placement is desired.

An applied-film enrobed product produced by the registering, preferably rotary, die process described in greater detail below has a characteristic signature. That signature is a very slight thickening of coating 12 along seam line 15; see FIGS. 3, 4, 8, 9, 11 and 12. Principally for aesthetic reasons, it is preferred that seam line 15 lie in the major 16 or secondary 16' plane of symmetry of the core of a medicinal or similar product according to this invention. Coincidence of the seam line with a plane of symmetry is particularly preferred where the applied-film enrobed product is bicolored (see product 18 in FIG. 6) for any one of various reasons including product identifiability.

Figure 25:
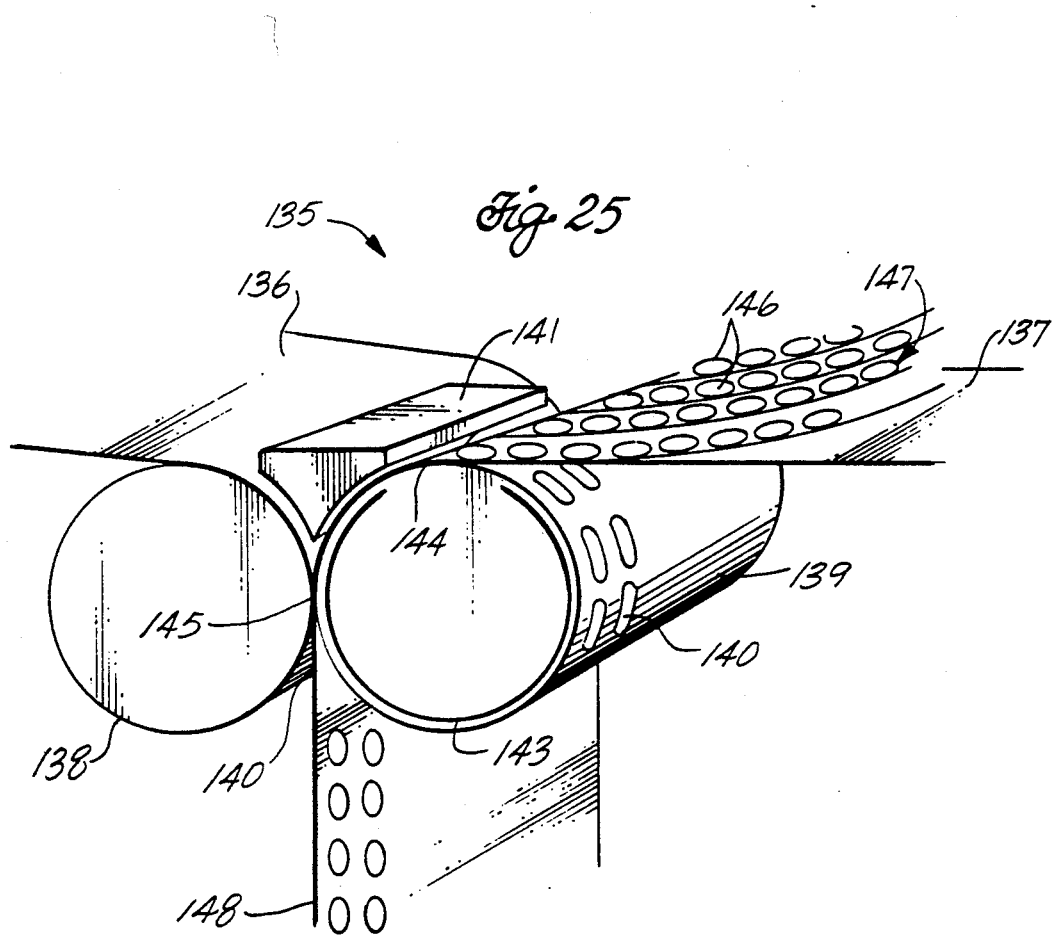
FIG. 25 is a simplified, fragmentary, perspective view of a further tablet feeding and die arrangement which can be used in the practice of this invention.

FIGS. 13 through 23 illustrate the presently preferred process for making applied-film enrobed articles according to this invention including the various kinds of medicine tablet products shown in FIGS. 1 through 12. FIGS. 13 through 23 also show presently preferred equipment useful to practice the preferred manufacturing method. Except for the nature of the core feeding mechanism, the basic aspects of the preferred process and manufacturing equipment are shown in FIG. 13 which is relevant to both the prototype and production apparatus more specifically discussed below. The manufacturing process and equipment create and use first and second films 36 and 37 of soft elastic gelatin of selected thickness and composition, and a pair of matching dies 38 and 39 (which preferably are rotary dies) and between which films 36 and 37 pass adjacent the location where a core feed device 40 cooperates with at least one and preferably both of the films and dies. That is, as shown in FIGS. 24 and 25, products according to this invention can be made by use of appropriately arranged apparatus pursuant to processes in which the product cores are initially engaged with only one of the two films before the films come together between matching dies. However, in the presently preferred embodiments of the manufacturing process and the manufacturing apparatus aspects of this invention, the core feeding mechanism is arranged to introduce the cores to the films in the working area between the dies so that each core contacts both films essentially simultaneously.

Workers skilled in the manufacture of soft elastic gelatin capsules and in the design and operation of machinery for making such capsules will readily appreciate that the general illustration of FIG. 13 is also broadly relevant to such processes and machinery as they now exist in some forms. Therefore, except for the specifics of the dies and the core feeding mechanisms used in the practice of this invention, the machinery and processes depicted in FIG. 13 will be familiar to such workers.

As shown in FIG. 13, films 36 and 37 are individually cast on separate rotating casting drums 42 and 43 in a continuous manner by introduction of liquid gelatin to the outer casting surface of each drum from a liquid gelatin dispensing device 44 of known nature and to which the suitably prepared gelatin of appropriate formulation is supplied. Liquid gelatin is supplied to each dispensing device from a respective container 45 in which the gelatin is kept liquid at an elevated temperature by a heater 46, such as an electrical heater. Each container 45 is airtight so that liquid gelatin can be moved from the interior of the container to the adjacent gelatin dispensing device 44 through a transfer tube 47 under the effect of compressed air introduced to the container through an inlet tube 48. Gravity feed of liquid gelatin to the dispensing devices can be used, if desired.

Each casting drum 42, 43 is cooled by circulation of an appropriate coolant as a result of which the casting surface of the drum is substantially colder than the liquid gelatin as introduced to the surface of the rotating casting drum by dispensing device 44. Hence, the liquid gelatin introduced to the moving casting surface as a layer of gelatin of predetermined thickness solidifies on the drum casting surface sufficiently to form film 36 or 37 adequately that the film can be led continuously from the respective casting drum to dies 38 and 39 along a desired path. The path of movement of the cast gelatin film is through a lubricant bath 50 via a roller 51 and thence to a driven tractor roll 52. The lubricant in bath 50 is applied in the bath principally to the reverse surface of the film, i.e., the surface of the film which will not be contacted with the other film when the two films come in contact with each other between die rolls 38 and 39. The outer surface of tractor roll 52 preferably is enwrapped by a traction layer 53 in the form of a sleeve of elastomeric mesh which enables the traction layer to co-act without slippage with the reverse surface of the gelatin film passing over the traction roll despite the presence on that film surface of a thin layer of lubricant. Thus, as the gelatin film passes from each tractor roll to the adjacent die 38 or 39, a thin layer of lubricant remains on the reverse surface of the gelatin film to function between the film and the cooperating die to prevent the die and the film from sticking to each other as the die operates upon the film engaged with it in the manner described more fully below.

As shown in FIG. 13, in the presently preferred process and equipment according to this invention, dies 38 and 39, together with the cooperating portion of the core feed mechanism 40, are symmetrically disposed relative to each other about a functional center plane 54 of the apparatus. The portion of the core feed mechanism immediately adjacent to the cooperating dies is a core feed horn 56 disposed upon functional center plane 54 in association with and between a pair of shaped metal heater blocks 57 which extend across the width of the adjacent gelatin film. Each heater block preferably includes therein an electrical resistance heater element 58 (see FIG. 19) for controllably heating the heater block. The heater blocks are provided in close proximity to the core feed horn 56 and to the die rolls for contacting the obverse surface of the adjacent gelatin film in that portion of the film path where the film preferably then is wrapped around the adjacent die roll. The heater blocks heat the gelatin film obverse surface to a desired temperature which is important to the topics of self-timing operation of the dies and feed mechanism and of the character of the enrobement of each product core by the gelatin films, both topics being discussed in greater detail below. Accordingly, as shown in FIG. 19, each heater block 57 has a curved film-contacting surface 59 configured for contact with the obverse surface of the moving gelatin film as it conforms to the outer diameter of the adjacent preferably rotary die as closely as possible to the point at which individual product cores emerge from the lower end of the wedge-shaped lower portion of core feed horn 56 substantially at the nip of dies 38 and 39. The die nip is the place where films 36 and 37 are brought into contact with each other by the dies, i.e., the place along the film paths where the dies coact with each other to enrobe the tablet cores (product preforms) with the gelatin films, to seal the films together around the individual cores, and to cut the enrobed cores from the film which are then mated to each other. Forms of film heating arrangements different from those described above can be used, if desired.

At the location in the apparatus shown in FIG. 13 where die rolls 38 and 39 and core feed horn 56 cooperate closely with each other, the product cores are individually contacted with the controllably heated obverse surfaces of the converging gelatin films 36 and 37. The films are stretched around the opposite sides of the cores symmetrically relative to apparatus center plane 54, thereby to define the applied layers 13 and 14 of the coating 12 of the desired product. The gelatin films are sealed to each other along the seam line 15 of the product and the thus conjoined and adhered films are cut to allow the gelatin enrobed products (shown as articles 60 in FIG. 13) to separate from a perforated gelatin web 61 which emerges from between dies 38 and 39. Web 61 is formed by the adherence of gelatin films 36 and 37 to each other by the dies. After emerging from between the dies, the web passes between a pair of driven mangle rolls 63 which have surface speeds slightly greater than the surface speeds of dies 38 and 39 so that web 61 is stretched between the dies and the mangle rolls. This stretching of the web as it exits from between the dies enables the gelatin enrobed product cores, i.e., products 60, to self-separate from the web and to move, with the assistance of product guides 64 (cooperating with the web between the dies and the mangle roles), into product receptacles 65 where the products are collected before undergoing such further processing as may be necessary. Further processing steps may include washing of products 60 to remove any residues of lubricant applied to the gelatin films in baths 50, final drying, or perhaps application to the products of timed release or enteric release coatings as appropriate.

The web 61 emerging from mangle rolls 63 is collected in a receptacle 66. The web material gathered in receptacle 66 is edible waste by-product of the manufacturing process. It may be reprocessed in the creation of further liquid gelatin material brought to the production machinery in containers 45, or it may be sold for use in other kinds of manufactures, such as livestock feeds or feed supplements, for example.

The upper edges of product guides 64 can define between them a narrow gap between which web 61 passes. If any items of product 60 have not self-separated from web 61 upon emergence of the web from dies 38 and 39 due to the tension created in the web by mangle rolls 63, then the upper edges of the guides engage any such unseparated products and cause them to separate from the web and to pass to one or the other of the two product collection receptacles 65. Other kinds of devices, such as brushes, can cooperate with web 61 between the dies and the mangle rolls to separate from the web any items of product which do not self-separate from the web.

As noted above, workers skilled in the art to which this invention pertains will readily appreciate the similarities between the production procedures and equipment illustrated in FIG. 13 and the production procedures and equipment well known and long used in the manufacture of soft elastic gelatin capsules filled with such flowable materials as cod liver oil, vitamin E, and the like. Such workers therefore will appreciate that the surfaces of dies 38 and 39 centrally of the axial lengths of those dies define a plurality of rows of uniformly spaced cavities, each row extending circumferentially of the respective die. Dies used in the volume production of soft elastic gelatin capsules filled with flowable material have multiple rows of cavities in their circumferences. Dies used in the practice of this invention for volume production of gelatin enrobed, unitary core products may have any number of cavity rows defined on them. However, for purposes of developing the manufacturing processes, and equipment which are aspects of the present invention, smaller scale prototype equipment was developed and successfully used. That prototype equipment included rotary dies having only three rows of cavities defined about their circumferences. Certain of the structural aspects of this invention are illustrated in the accompanying drawings with reference to dies which have only three rows of cavities in them. Workers skilled in the art will appreciate that such illustrations disclose principles and structural arrangements which can be expanded to dies having any number of rows of cavities desired.

The details of dies 38 and 39 as configured for use in the presently preferred process and equipment according to this invention are more fully described below with particular reference to FIGS. 19 through 22.

FIG. 14 generally illustrates a preferred core feeding mechanism 40 useful with and as a part of the equipment shown in FIG. 13. Feeding mechanism 40 includes a first stage core feeder 67, an intermediate feeder 68, and a final feeder 69 of which core feed horn 56 is a component. The intermediate feeder and most of the structure of final feeder 69 are located in an enclosure 78 which has an inlet opening 76 in its top. First stage core feeder 67 includes a hopper 70, preferably having a closable cover 71, into which large quantities of cores for products to be film enrobed are introduced. Hopper 70 discharges cores therefrom to intermediate feeder 68 via a discharge 72 from the hopper. To facilitate the discharge of cores from hopper 70 to the intermediate feeder, the hopper is secured to a support 73. A vibrator 74 is connected to the bottom of hopper 70 to agitate cores in the hopper so that cores emerge as desired from hopper discharge 72 to pass through opening 76 in the top of enclosure 76; any other suitable mechanism desired can be used to load cores into enclosure 77. Where the products produced are to be film enrobed medicine tablets and the like in which it is desired that the applied film coating on each tablet tightly adhere to the tablet surfaces, it has been found to be important that the tablets, when finally introduced to contact with gelatin films 36 and 37, are as free of excessive dust particles as possible. It has been found that the presence of dust particles on the tablet cores or on the obverse surfaces of the gelatin films applied around the tablet cores is undesirable. The presence of excessive dust particles on the film obverse surfaces can result in imperfect sealing of the applied gelatin layers 13 and 14 to each other. Therefore, dedusting procedures are practiced in association with the intermediate and final stages of core feed mechanism 40.

The discharge 72 of hopper 70 leads to an inlet 76 below which is an open top intermediate feeder box 77 movably mounted in the upper portion of a dust-containment enclosure 78. The principal function of intermediate feeder 68 is to load individual product cores into a plurality of core downtubes 79 which connect to respective vertically disposed core passages 80 formed within core feed horn 56. Such loading of cores from box 77 to downtubes 79 is achieved by laterally shaking or vibrating box 77; this is accomplished by coupling the box to a stationary support bracket 81 via a suitable shaker drive device 83. The support bracket is inside enclosure 78 which is, in turn, mounted in any convenient way to a foundation 82. Preferably, the amplitude of oscillation of box 77 is greater than the amplitude of oscillation of the bottom of hopper 70. The upper ends of core downtubes 79 connect to the bottom of box 77 via suitable openings 85 as shown in FIG. 18. Dust either introduced to the interior of box 77 with the cores or generated within the box by agitation of the product cores is extracted from the interior of enclosure 78 through a duct 88 which is connected to a suitable source of vacuum.

Downtubes 79 are located within enclosure 78. Since box 77 is oscillated laterally relative to enclosure 78, downtubes 79 are flexible. The upper ends of the flexible downtubes connect to the bottom wall of box 77 around respective ones of openings 85, see FIG. 18.

The presently preferred form of each core downtube 79 is a length of tubular, helically wound spring, the inner diameter of which is sufficiently large to enable cores such as caplets to move readily along the lengths of the downtubes and into respective ones of passages 80 to which the lower ends of the downtubes are coupled. To facilitate dedusting of cores moving through downtubes 79, the helical springs used to define the downtubes are not tightly wound but rather, as shown in FIGS. 17 and 18, are defined with slight spacing between adjacent turns of the spring helix. Also, to enable the cores to move as desired along the downtubes, it is preferred that at least the inner surfaces of each downtube be coated with a material having a low coefficient of friction, such as tetraflouroethylene.

It has been found that caplets, because of their geometry, feed best from box 77 to downtubes 79 when the openings 85 through the bottom of box 77 to the respective downtube are conically flared, concave upwardly, in the manner of a funnel as shown 87 in FIG. 18. It will be apparent that the size and geometry of the surfaces defining the openings from box 77 to the respective core feed downtubes are defined as a function of the geometry of the cores which are to be handled. Thus, the dimensions and geometrical aspects of the final stage core feeder and of the interface between the intermediate and final core feeders, and the similar aspects of final feeder 69, are defined with reference to the particular cores which are being fed. These aspects will be different when the cores being fed are caplets, as compared to the cores for products 27 and 33 shown in FIGS. 7 and 10, respectively.

Dust particles carried by cores moving through downtubes 79 and dislodged from the cores during such movement are extracted from the interior of enclosure 78 through duct 88.

In the development of this invention, various tablet sizes and configurations were handled in the development of core feed mechanisms 40. Caplets weighing from 600 mg. to 700 mg. and sized at from 0.68 to 0.80 inches long, 0.256 to 0.284 inches wide, 0.230 to 0.260 inches high and having a diagonal (dimension D shown in FIG. 2) of 0.29 to 0.32 inches were used. Cylindrical, round-ended tablet cores weighing from 590 to 660 milligrams and with dimensions of 0.70 to 0.80 inches in length, 0.24 to 0.26 inches in diameter, and 0.25 to 0.27 inches diagonal across the nominal cylindrical peripheral surface thereof were also used. Round cores (see FIGS. 7 and 8) weighing from 290 to 560 milligrams, 0.210 to 0.410 inches in diameter and 0.170 to 0.225 inches thick were also handled. In handling all of these different cores, an objective was to cause the seam line 15 between the applied gelatin layers of the finished enrobed cores to lie in either the major plane of symmetry 16 of the core or the secondary plane of symmetry 16' of the core. It was found, particularly in the instance of caplet cores, that particular attention had to be given to the handling of the cores in the final core feeder to cause the cores to be properly aligned relative to the dies. Such alignment was found to be important to the desired coincidence of seam line 15 with the core major plane of symmetry. It was found that causing the core downtubes to be sloped, rather than vertical, over a portion of their lengths between the intermediate feeder and the top of core passages 80 significantly improved the probability that caplet cores would have proper alignment with the die cavities upon contacting the gelatin films as the caplet cores emerged from the lower ends of passages 80. To assure that all tablet cores are properly aligned as they emerge from the lower end of core feed horn 56, it is preferred that a core alignment mechanism be incorporated into the core feed horn 56 for cooperation with the cores as they move downwardly through passages 80. Such a mechanism 90 is shown generally in FIGS. 14 and 15, in more detail in FIG. 16, and in greatest detail in FIG. 23. Mechanism 90, as illustrated, is arranged to cause cores introduced to the nip of dies 38 and 39 to have their major planes of symmetry 16 aligned with the die nip line so that the seam lines 15 between the applied film layers on the finished products lie substantially in the major plane of symmetry of the product cores. The principles of mechanism 90 can be used to provide a core alignment mechanism useful to cause tablet cores to have their secondary planes of symmetry 16' aligned with the die nip line.

Figure 23:
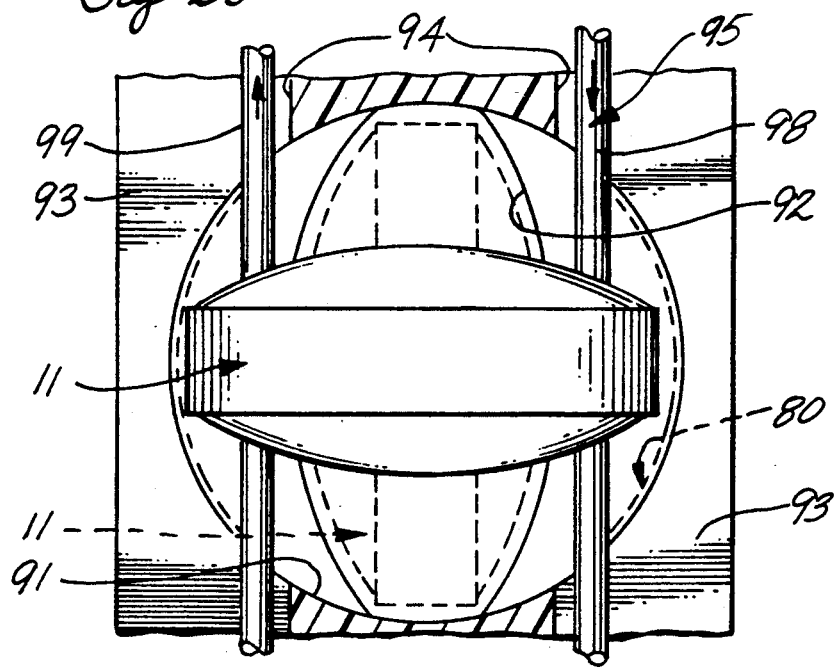
FIG. 23 is a simplified top plan view of a portion of a presently preferred mechanism for achieving proper positioning of caplet-style tablets in the final stage tablet feeding mechanism shown in FIGS. 15 and 16.

An upper portion 91 (see FIG. 23) core passage 80 in core feed horn 56 has a circularly cylindrical configuration. A lower portion 92 of each passage has a cross-sectional configuration with the same shape as, and is slightly larger in dimension than the cross-sectional configuration of the core of interest. The configuration of the passage lower portion is oriented in horn 56 so a core in that passage portion is aligned with its major plane of symmetry parallel to and midway between the axes of rotation of dies 38 and 39. The location of the transition between the circular and core-contoured portions of the length of each passage 80 is at a common height along the lengths of the passages. Preferably that transition is located above the location where heater blocks 57 are mounted in cooperation with the feed horn. As shown in FIGS. 16 and 23, the outer side surfaces of the feed horn which are disposed parallel to the axes of rotation of the adjacent dies are recessed 93 at this location to a depth such that the vertical base surface 94 of each recess intersects the circularly cylindrical upper portion 91 of each core passage 80. However, the recess depths are defined so that the plane of surface 94 of each recess lies outwardly of the core-contoured lower portion 92 of each passage 80. That is, the elongate recess 93 formed in each side surface of core feed horn 56 intersects the lowermost portion of the circularly cylindrical upper portion 91 of each passage 80, but it does not have a depth sufficient to extend to the adjacent wall of the core-contoured lower portion 92 of each passage.

A belt 95, which preferably is defined by a suitably sized rubber O-ring, is engaged between a pair of support pulleys 96 disposed one adjacent each of the opposite ends of the core feed horn in the plane of recesses 93. Between the pulleys, the opposite parallel legs 98 and 99 of the belt loop are disposed in recesses 93 sufficiently close to the recess vertical surfaces 94 that they pass in chordlike manner across diametrically opposite parts of the lower portion of the circular upper part of each passage 80 and so that the spacing between the opposite belt loop legs is less than the width of caplet core 11, e.g. A shaft 100, to which one of pulleys 96 is mounted, is rotated in a desired direction by operation of a motor 101 suitably mounted adjacent the core feed horn and to which the shaft is coupled in an appropriate manner. During times when core feed mechanism 40 is operated, motor 101 is also operated. Accordingly, belt 95 has one of its legs 98 moving in one direction across one outer portion of the lower end of the circular part of each passage 80 and has its opposite parallel leg 99 moving in the opposite direction across an opposite outer portion of the same part of the same passage.

As shown in FIG. 23, if a caplet core 11 approaches the upper end of core contoured portion 92 of passage 80 aligned transversely of the major dimension of the cross-sectional shape of the passage lower portion, it cannot enter the passage lower portion. However, as such a misaligned caplet core approaches the passage lower portion 91, it engages the oppositely moving legs 98, 99 of belt 95 and, because of the opposite directions of motion of the belt legs, is turned about its length in passage upper portion 91 until it is angularly positioned so that it can enter passage lower portion 92. As the caplet is turned in the circular part of passage 80 so that it can enter into the lower portion of the passage, it quickly disengages itself from contact between the oppositely moving belt legs and quickly passes between those belt legs into the passage lower portion. The dimensions of the passage lower portion are slightly larger than the cross-sectional dimensions of the caplet core so that the core can move freely under the bias of gravity and other influences downwardly through passage portion 91 while being confined by cooperation with the shape of the passage lower portion to have its major plane of symmetry parallel to and substantially coincident with the major plane of symmetry of the passage lower portion. It follows from the preceding description that when the caplet emerges from the lower end of passage 80 into contact with gelatin films 36 and 37, the major plane of symmetry of the core will lie substantially in the plane of symmetry 54 of the enrobing apparatus. As enrobed by the gelatin films, the caplet or other tablet core will have the seam line 15 between the layers of gelatin applied to it substantially coincident with the core major plane of symmetry 16.

If the products 60 to be produced in the enrobing apparatus are to have their seam lines 15 between applied film layers 13 and 14 lying in the secondary planes of symmetry 16' of the cores, then a suitably defined different core alignment mechanism can be used. For example, in such a different mechanism, the passage lower portions 92 could have the same shape as shown in FIG. 23 but with their major cross-sectional dimensions turned 90° from the orientation shown in FIG. 23. Instead of a belt common to all passages 80 in the core feed horn, a separate belt can be used at the transition between the upper and lower portions of each passage 80, and each belt can be mounted on a respective pair of pulleys located in or adjacent to recesses 93 so that the legs of each belt loop runs between the recesses at locations spaced equivalently to the spacing between legs 98 and 99 of belt 95. A further belt, disposed and driven similarly to belt 95 but with its parallel legs located outside the several passages 80 can be used to drive one or both of the pulleys mounting each of the several belts extending between recesses 93.

Thus, film enrobed medicine tablets having seam lines 15 aligned with either the major 16 or secondary 16' planes of symmetry of the tablets can be provided as the products of this invention.

It has been found that while the height of a column of tablet cores in a passage 80 is a factor affecting the unclocked, self-timing manner in which cores are dispensed into contact with gelatin films 36 and 37 at the nip of cores 38 and 39, the presence or absence of core alignment mechanism 90 along passages 80 appears to be immaterial to the feeding mechanism. The height of such column for effective creation of the automatic core-to-film feed mechanism in the presently preferred arrangement shown in FIG. 19 appears to be definable independently of the presence or operation of mechanism 90 so long as such mechanism, if present, is operating. The core alignment mechanism operates so quickly in a tangential manner upon cores in passages 80 that the mechanism has no discernible effect upon the free movement of cores along the passages under the influence of gravity and the height and weight of the core column.

In the prototype apparatus referred to above, core feed horn 56 was fabricated from clear plastic so that the movement and behavior of the various product cores within passages 80 could be observed. A layer of thermal insulating material 103 can be placed between each horn side surface and the adjacent heater block 57 to protect the plastic feed horn from the adverse effects of the temperatures created by operation of the heater elements 58 in the heater blocks. It is within the scope of this invention, however, that all or at least the lower portion of the core feed horn can be defined of metal. In that event, the heater elements preferably are disposed in the upper portion of the wedge-shaped lower part of the horn with the lower portions 92 of the several passages 80 passing between the positions of the heater elements to their openings at the lower extremity of the horn wedge. Such an arrangement is shown in FIG. 16.

FIG. 16 also shows that, as preferred, a switch 104 can be mounted to the core feed horn in association with each passage 80 for blocking the passage at a desired location along its length. Preferably that location is below the location of the belt 95. The switches can be bistable electrical or pneumatic devices which, when in one state, allow a plunger to extend sufficiently into the cooperating passage 80 to prevent the movement of cores through the passages, but which, when in the other state, cause the plunger to be withdrawn from the passage.

FIGS. 19 through 22 show details of the drum-like dies 38 and 39 which are used in the preferred procedure and machinery according to this invention for producing the preferred product 10 of this invention. Dies 38 and 39 are essentially identical. Each die is arranged to be rotated about an axis. Die 39 is positively driven at a desired angular velocity, and die 38 is slaved to driven die 39 by gears (not shown) between the dies so that dies 38 and 39 rotate synchronously in opposite directions about their respective axes of rotation. Since dies 38 and 39 are identical, except to the extent described above, a description of die 39 shall constitute a description of both dies.

Die 39, as shown in FIG. 20, has a circularly cylindrical working surface 107 extending along the length of the die drum between its opposite ends. There are defined in working surface 107 a plurality of recesses 108 each of which cooperates with a corresponding recess in the other die for defining a corresponding cavity between the dies as they turn about their axes of rotation into and out of substantially matching coaction with each other. The cavities defined by cooperation of the respective die recesses are sized and shaped to loosely receive in each cavity a single article preform, such as a caplet 12, which serves as the core of the product 60 which emerges from between the dies as will be shown below. That is, while the several recesses in the working surfaces of the dies are identical and are sized and configured with reference to the particular article preforms related to the dies, those recesses are oversized relative to the preforms so that, even as enwrapped and enrobed between films 36 and 37 within each cavity formed by cooperating recesses, the preform and films within the cavity are loose within the cavity and do not bottom-out or otherwise significantly contact the bottom or sides of the recesses. Since, as shown in FIG. 19, dies 38 and 39 are used to produce products 10 which have caplet cores, the planform configuration of each recess 108 in each die has a geometry which corresponds to the top plan view of product 10 as shown in FIG. 1 but is somewhat oversized in width, length and depth relative to such product. Each recess 108, as formed in a die working surface 107, is surrounded by a raised rim 109, the end of which is spaced from the adjacent die working surface and which makes essentially direct contact with the corresponding feature of the adjacent die as the dies turn synchronously about their respective axes. The edges of each recess rim, both toward and away from the corresponding recess, are rounded to desired small radii of curvature.

Figure 21:
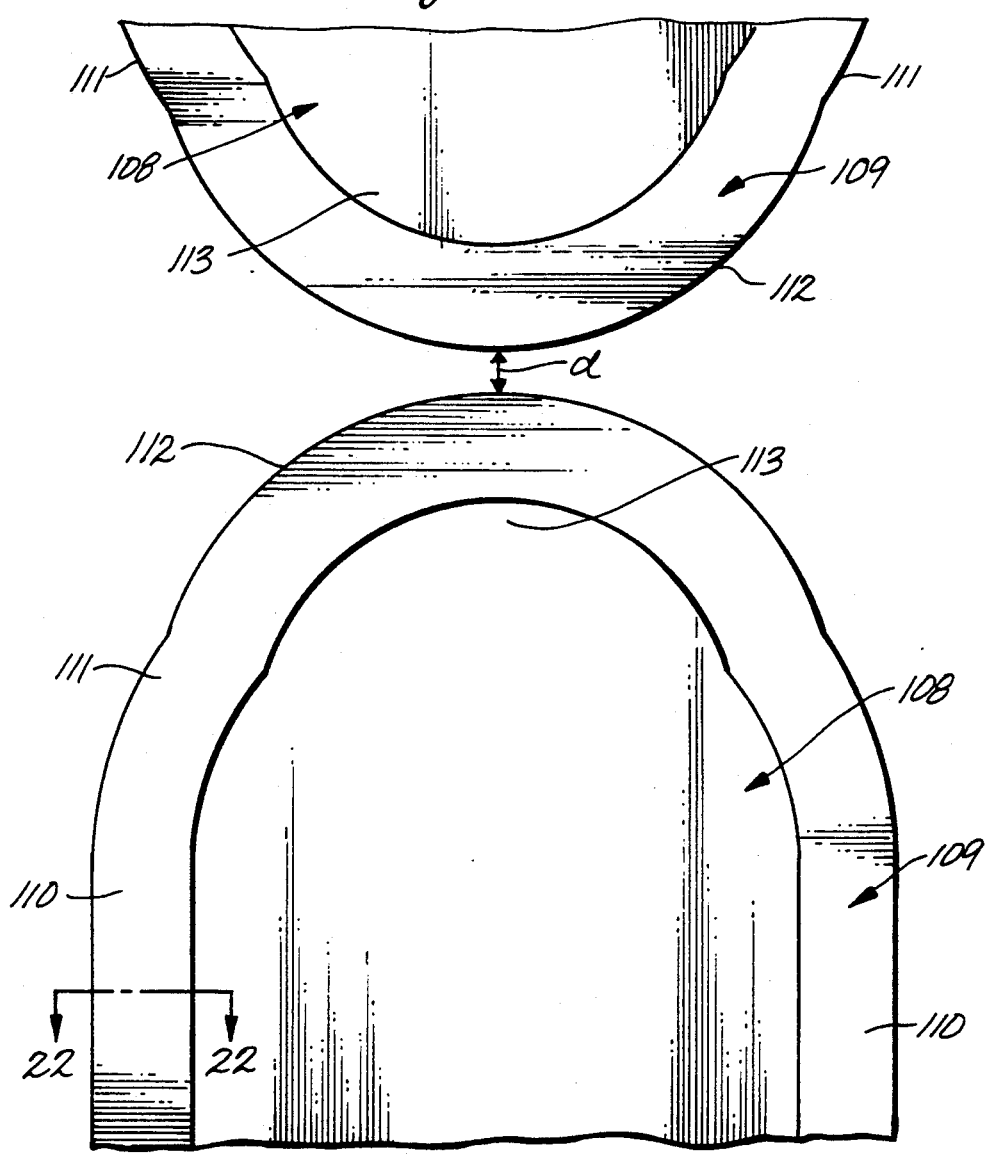
FIG. 21 is a fragmentary, enlarged plan view of a presently preferred cavity and land configuration useful in the die rolls shown in FIG. 20.
Figure 22:
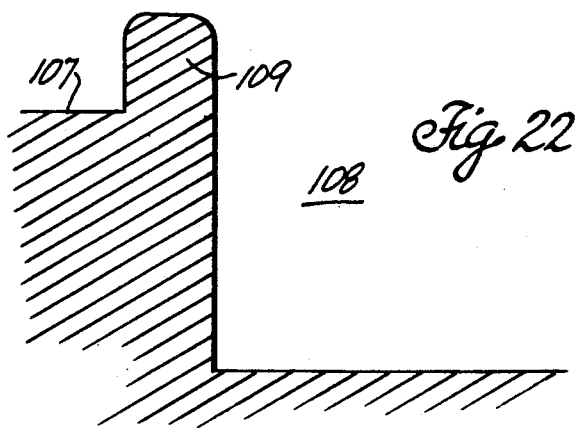
FIG. 22 is an enlarged cross-section view taken along line 22—22 in FIG. 21.

Consistent with the foregoing, each rim 109 of a recess 108 for use with caplets 12 has parallel opposite sides 110 aligned with the circumference of die 39 and arcuately configured portions 111 at each of the opposite ends of cavity 108 see FIG. 21. For reasons which are described more fully below, the rounded end portion 111 of each cavity rim 109 has a base curvature in which the radius of the arc of the rim is substantially equal to one-half the width of cavity 108 between straight rib portions 110. At the extreme ends of each recess 108, a more curved arcuate portion 112, having a smaller radius of curvature, is centered on the elongate center line of the recess. The more curved portion 112 of the peripheral rim around each recess provides a supplemental volume (relief) 113 at each end of the recess; this additional volume is supplemental to that which would be provided in the recess were the recess rim end portion 111 of entirely semicircular planform configuration. The end of each recess rim 109 spaced away from die working surface 107 is a land surface in the die.

The supplemental volume at each end of a die recess can have a geometry different from that shown in FIG. 21, if desired. For example, the supplemental volume, when viewed along a line normal to the die working surface, can have a shape resembling a rectangle wrapped around the principal contour of the recess end. The supplemental volume shape which is most effective may and likely will vary with the shape and dimension of the core with which the die recess cooperates in any given instance. The principal significance of the supplemental volumes in a die recess is to assure that, in cooperation with the size and shape of the relevant article preform being handled at any given time and the orientation of that preform relative to the recess, the area of film disposed over the recess within the recess rim, at the time the die moves in conjunction with the other die to close the recess around the preform, is an area which is sufficient, in connection with the thickness, composition and condition of that film, to accommodate stretching of the film in all directions, without rupture of the film, to fully cover the preform in conjunction with the action of the film overlying the matching recess in the other die.

As shown in FIG. 20, a plurality of rows of recesses 108 are provided circumferentially of die 39. The rows are uniformly spaced from each other, center-to-center, along the axial extent of the die within the central portion of the length of the die. In each row, the recesses are spaced at uniform intervals around the circumference of the die with a preselected spacing "d" (see FIG. 21) between the outer portions of recess rims 109 along the line of each row of recesses. Distance "d" is a relatively small distance; it is as small as workable consistent with the functioning of lands 109 to seal films 36 and 37 around individual preforms and to cut the film-enrobed preforms, with their gelatin enrobing layers sealed to each other, from web 61. Web 61 is created as films 36 and 37 converge and are squeezed together as the films move through the place where dies 38 and 39 have their closest cooperation with each other; that place is a line parallel to the die axes where the dies substantially register with each other. Distance "d" preferably is determined with reference to the thickness of the films passing between the dies.

If desired, dies 38 and 39 can be hollow and recesses 108 can be defined as holes through the cylindrical shell of each die.

As shown in FIG. 20, two rows of teeth 115 are raised from die working surface 107 circumferentially of the die at each end of the die. The teeth on one die do not intermesh with the corresponding teeth on the other die in the manner in which the teeth of meshed gears interdigitate with each other. Teeth 115 comprise traction tires on the ends of each die for gripping the respective gelatin film which has a width transversely of the film web greater than the axial length of the drum. The clearance between the teeth on the two dies at the line of die registration is less than the combined thickness of films 36 and 37. Thus, the teeth grip the films and cause die 38 to rotate synchronously with driven die 39 through the agency of the films engaged between the dies In view of what has been stated above, it will be apparent that die 39 as shown in FIG. 20 with three rows of recesses 108 about its central circumference, corresponds to the dies for the prototype equipment used in the development of this invention. Workers skilled in the relevant art will readily appreciate that, in production machinery, dies having the character described above but having more than three rows of dies about their circumference can be used and likely will be preferred. It will be noted that, as described above and as shown in the accompanying drawings, it is presently preferred that recesses 108 have their long dimensions aligned with the circumference of the dies rather than with the axial extent of the dies. This orientation of the recesses on the die working surfaces is consistent with the presently preferred end-wise feeding of caplets 12 to the nip between dies 38 and 39 in the manner shown most clearly in FIG. 19.

As will be appreciated from an inspection of the illustrations of FIG. 19, caplets 12 are individually dispensed in a passive, unclocked, self-timed manner into simultaneous contact with the heated obverse surfaces of gelatin films 36 and 37 substantially at the nip between dies 38 and 39 where they cooperate most closely with each other. The caplets emerge one at a time from the lower end of a lower portion 92 of a core passage 80 in core feed horn 56; there is one passage 80 for each row of recesses around a die. Each passage 80 has its centerline defined to intersect the centerline of the corresponding two rows of recesses 108 in the adjacent dies 38 and 39. As stated above, passages 80 are aligned along the functional center plane 54 of the core enrobing apparatus. Passages 80 open to the die nip area through the substantially knife-edged lower end of the wedge-shaped lower portion of the core feed horn. In each passage 80, caplets 12 are disposed lengthwise in end-to-end relation to each other in a caplet column in which each caplet stands on the caplet below it in the passage. The caplets in the lower portion 92 of each passage 80 have their major planes of symmetry 16 aligned with apparatus center plane 54 for the reasons described above with reference to FIG. 23.

The frequency at which individual caplets 12 emerge from the lower end of each passage 80 is a frequency which is self-defined within the enrobing apparatus and is the same frequency at which cavities 108 pass the place of closest cooperation between the dies in response to rotation of the dies. It has been found that there are several things which affect this unclocked dispensing of caplets and other tablet cores to films 36 and 37 and to the rotary dies around which the gelatin films are wrapped in the vicinity of and below the core feed horn. These factors include the composition of the gelatin material from which films 36 and 37 are cast, the thickness of films 36 and 37, film elasticity, film temperature at the point of contact of each core with the films between the lower extent of the feed horn and the die nip, the tension in films 36 and 37 across recesses 108 as the films are engaged by each core, the adhesiveness of the films to the dispensed cores, core mass and size, the number of cores in the column of cores in each core passage 80, and the rate of advance of films 36 and 37 past the lower tip of the core feed horn. These factors are interrelated to each other with greater or less degrees of directness.

The relevant film advance rate is determined by the surface velocity of the rotating dies 38 and 39. Pertinent tension in the films is determined, among other ways, by the difference in surface velocities of the dies as compared to tractor rolls 52. The surface velocities of the dies are defined to be a selected slight amount greater than the surface velocities of the tractor rolls. Another factor affecting film tension is the temperature of the film as determined by the quantity of heat transferred by each of heater blocks 57 to the respective films. Film elasticity is interrelated to the film composition, the film thickness and the film temperature. The extent to which the film obverse surfaces adhere to the cores is a function, among other things, of the film surface temperature. It has been found that, for cores of given mass, size and shape, there can be too few or too many cores in the core column within passage 80 for the self-timing aspect of the core-to-film feed operation to be achieved satisfactorily. In other words, one of the factors which affects the unclocked, self-timed dispensing of cores to films 36 and 37 from passages 80 is the static head of cores in the passages. These various factors and their interrelationships are discussed more fully below.

Particularly in the instance of caplet cores, it has been found important to the successful realization of the self-timed core dispensing effect to provide the supplemental volumes 13 at the ends of die recesses 108. Caplets have been found to be a difficult configuration of core in the context of the self-timed dispensing effect. Round cores, or cores which are more round than they are of caplet configuration, such as cores for products 34 (see FIG. 12), are more readily handled than caplets in the unclocked core dispensing arrangement shown in FIG. 19.

It has been found that, when the various factors and influences described above are properly observed in relation to each other, tablet cores, even cores of caplet configuration, can self-feed satisfactorily into contact with films 36 and 37 without positive injection of the cores to the films and without other metering procedures being observed. When these factors and influences are observed, it has been found that the lower end of the lowermost core in passage 80 effectively contacts films 36 and 37 at a location on the films where the films overly die recesses positioned at about the position of recesses 108' illustrated in FIG. 19. The gelatin film obverse surfaces, being sticky by virtue of heat having been applied to the films from heating blocks 57, grab a core from the lower end of passage 80 and carry the grabbed core with the films away from the lower end of the core feed horn. As this occurs, the films stretch around the grabbed core within the corresponding recesses and, particularly where the presently preferred gelatin formulation described above is used, conform closely to the contours of the grabbed core and adhere to the core. Because each core is introduced into contact with the films with the major plane of symmetry of the core aligned with apparatus center plane 54, the films apply themselves to the core symmetrically about the core major center plane 16 and form a seam line 15 around the core at a location on the core which is essentially coincident with that major plane of symmetry. All of these things occur as the dies continue to rotate following first contact of each core with films 36 and 37. As a core enrobed between the gelatin films reaches and passes through the point of closest contact of the dies with each other, the films surrounding each core are sealed tightly together. Such sealing occurs due to the self-adhesive nature of the films to each other by reason of the heat applied to the films at heater blocks 57. Essentially concurrently with sealing of the films tightly together thereby to define web 61, the lands defined by the ribs 109 which surround each cavity 108 move into sufficient proximity to each other to cut the enrobed cores from the web. The cores, as fully enrobed by applied gelatin film layers sealed to each other around the periphery of the core, can either fall from the web or be forcefully extracted from the web in the manner described above as each such core emerges from between the dies below the point of closest cooperation of the dies with each other. At that point, products according to this invention are essentially completely enrobed and lend themselves to washing and further drying operations, and perhaps further processing and treatment coating operations, as may be desired.

The thickness of films 36 and 37 is a factor, among others, which affects the resiliency of the gelatin films during the core enrobing process. The stretchability of film over a core is also affected by film thickness. The minimum film thickness which can be used for successful enrobement of cores is in turn affected by the type of gelatin used to create films 36 and 37 and by the gelatin-liquid formulation. In rotary die core enrobement apparatus of the kind described above, it has been found that films having a thickness of from 0.02 to 0.04 inches thick worked well, although films having a thickness of 0.01 inch were handled successfully. For practical purposes, it is believed that gelatin films thinner than 0.005 will require the use of a specialized casting system. As noted above, if equipment of definition different from that described above is used, films of lesser or substantially greater thickness can be handled.

It has been found that the unclocked self-timed dispensing of stacked cores from passages 80 to soft elastic gelatin films engaged over and between rotary dies of the kind described above is relatively unaffected by die velocity. Surface speed of the dies should not be so high as to exceed the ability of the cores in passage 80 to move under the bias of gravity into contact with the films passing the lower end of the core feed horn at a frequency which corresponds to the effective frequency at which recesses 108 pass the same place.

It has been found, particularly in the instance of caplet cores, that close spacing between adjacent recesses 108 in each line of recesses circumferentially of the dies, and the provision of supplemental volumes 113 in the ends of the die recesses, are significant to eliminate the tendency of the die structure between adjacent recesses .

from nipping at the lower ends of cores fed to films 36 and 37 through passages 80.

It has been found that the temperature of the gelatin films as they pass the lower end of the core feed horn is significant to the fluidity of the gelatin film and its ability to form a seal around cores dispensed to the films. The precise temperature which is best in any instance depends upon film thickness and the gelatin formula. Film temperature at and near the die nip is also affected by the geometry of the core feed mechanism in cooperation with the dies, and by how far from the die nip location the film heater blocks are located.

From experience with various gelatin formulations and film thicknesses, it has been found that the core feed wedge temperature is best controlled and maintained within a range of from 100° F. to 190° F. The precise temperature which is best used in any given instance depends upon the gelatin formula and film thickness. Temperature should be controlled within plus or minus 2° F. for optimum film sealing results.

Gelatin type, source, and formula have an impact upon film elasticity, the ability of the films to adhere to cores dispensed to the films, and the adhesion of the films to the dies. Gelatins with bloom values of from 150 to 180 are preferred, but it has been found that gelatins having a bloom value in the range of from 120 to 250 can be handled. Specific gelatins with blooms as high as 300 and as low as 100 can be custom manufactured.

The adhesion of the gelatin film to the product core is significant in two ways. In one way, adhesion of the film to a core produces a grabbing effect of the films upon the core to self-time the dispensing of cores onto the films. The other aspect of film adhesion is relevant during the product drying process where the applied gelatin layers forming the gelatin coating around the enrobed product becomes an integral part of the finished product and cannot, as presently preferred, be physically removed without damaging the core. This is particularly important where the product to be produced is a tamper-evident medicine tablet. It has been found that where the ratio of plasticizer to gelatin in the initial gelatin formulation is about 1:5, a very satisfactory tamper-evident gelatin film enrobed tablet is produced. Gelatin films cast from gelatin formulations having gelatin to plasticizer ratios in the range of from 3:1 to 15:1 will adhere to most tablet cores. Low ratios of plasticizer to gelatin result in a brittle coating around the tablet core, while high ratios result in a gelatin coating around the tablet which is flexible and can be peeled from the tablet.

It has been found that substantially any gelatin formulation which can be used successfully in the manufacture of soft elastic gelatin capsules containing flowable materials such as powder, liquids or pastes, can be handled in the processes and apparatus of this invention to produce applied-film gelatin coatings around a wide range of cores or product preforms. In that context, gelatin formulations having by-weight compositions of 32 percent to 50 percent gelatin, 17 percent to 35 percent plasticizer, 29 percent to 44 percent water, and colorants and pigments in the range of from 0.1 percent to 3 percent can be handled. However, if a gelatin coating which adheres to the product core is desired, then gelatin formulations having by-weight compositions of 40 percent to 60 percent gelatin, 5 percent to 12 percent plasticizer, 35 percent to 50 percent water, and colorants and pigments in the range of 0.1 percent to 3 percent should be considered. Glycerin and sorbitol can be used as single plasticizers or in combination with each other. In addition, other sugars and poly-hydroxy compounds can be used as additives and plasticizers. If a tamper-evident gelatin-coated medicine tablet is the desired end product, then the ratio of plasticizer to gelatin in the gelatin formulation should be in the range of about 1:5. It will be appreciated that the range and versatility of gelatin film formulations which can be handled by the present technology makes possible the manufacture of gelatin coated tablets or other products which have peelable coatings, as where the applied film coating is desired around the product core to serve as a protectant or preservative for the core.

The present invention provides significant advantages over previously known techniques for gelatin coating medicine tablets and the like by dipping processes. In order for dipping processes to be practiced, the gelatin baths into which tablets and the like are dipped must be in a liquid state. That means that such gelatin baths must contain substantial unbound water which is free to react with the active or other ingredients in the medicine tablets. In the practice of the present invention, on the other hand, gelatin films exhibiting substantially low water activity are used to produce the desired gelatin coating around the medicine tablet core. In these gelatin films, the water molecules are significantly more bound to the other constituents of the film. The result is that there are few water molecules in the fluid which are free to react with the cores around which the films are applied. Also, applied gelatin films used in the practice of this invention are substantially cooler when they come into contact with medicine tablet cores than is the case of tablets dipped in gelatin baths which must be at relatively high temperature in order to have the requisite fluidity. Accordingly, medicine tablets coated with gelatin by the practice of this invention have the gelatin coatings applied to them in a substantially dry state and at materially lower temperatures so that the medicine tablet cores are significantly less adversely affected by the gelatin coating process than where a gelatin coating is applied to a medicine tablet by a dipping process. Further, because the layers of gelatin applied to medicine tablets or other product cores according to this invention can adhere tightly to the core surfaces over the whole of the core, this invention can provide products in which there is no air trapped between the applied gelatin coatings and the cores to oxidize the core or any of its constituents; in such instances, any air present in the product is air which was present in the core before application of the coating to the core.

While the presently preferred procedures and equipment for practicing this invention have been described above with reference to FIGS. 13–23, other procedures and equipment can be used to implement the invention. As shown in FIG. 24, in apparatus 120 a pair of suitably formulated films 121 and 122 of desired thickness can pass from suitable film casting devices or other film sources (not shown) around respective rotary dies 123 and 124 to a nip 125 between the dies past a film heater 126 which cooperates with the films as they wrap around the dies. The heater heats the films to a desired temperature determined with reference to the film compositions to create in the films the desired conditions of elasticity, surface tackiness and other desired characteristics. At least die 124, or both dies if desired, define recesses 127 in their circumferential working surfaces shaped and sized to cooperate in the manner already described with desired article preforms such as medicine caplets. FIG. 24 shows that recesses 127 can be elongated along the axis of the die to cooperate with caplets dispensed lengthwise relative to the dies. A preform dispenser 128 is associated with one of the films, e.g. film 122 near heater 126 on the side of the heater opposite from die nip 125, for dispensing preforms in a desired positional attitude to one of the films, e.g. film 122, such altitude corresponding to the manner in which the die recesses are formed. A film heater 129 is located ahead of the dispenser along the film to which preform dispensing occurs for heating the film before dispensing to a condition of sufficient surface tack that each dispensed preform adheres to the film to move with the film toward die nip 125.

Dispenser 128 comprises a plurality of preform magazines 130, one magazine for each row of recesses circumferentially of the die or dies. The magazines meter preforms to respective recesses in a preform transfer device 131 which in turn moves individual preforms to the adjacent film surface and places the preforms on the film surface at places on the film which correspond to respective die recesses. The film surface tack grabs the dispensed preforms and carries them with it under heater 126 which can also serve as a guide to hold the dispensed preforms on the film without altering the places occupied on the film by the preforms. The operation of dispenser 128 is synchronized to movement of the films and the dies by a suitable actuating mechanism, such as a timing belt 132 which cooperates between the transfer device and a roller 133 which rotates in synchronism with movement of one of the films.

An apparatus of the kind shown in FIG. 24 can operate in the die area in different ones of several ways, depending upon the nature of the preforms, the precise nature of the film enrobement of preforms which is desired, and other factors. If both dies 123 and 124 define recesses 127, the dies can cooperate in the same manner as dies 38 and 39 to produce enrobed products like or similar to those shown in FIGS. 1-12. If only one die defines recesses 127 and the other die does not, then the dies can cooperate to produce film enrobed products in which the applied film coating on each preform has the applied layers disposed asymmetrically about the preform.

Alternatively, an apparatus 135 (see FIG. 25) for making applied-film enrobed products moves a pair of films 136 and 137 around and between a pair of rotary dies 138 and 139 which have surface recesses 140 of desired size, shape and orientation at corresponding places on their outer surfaces. A film heater 141 cooperates between the dies with the films wrapped on the dies to heat the films for the reasons already described.

Die 139 is hollow and is evacuated inside its circumferential shell in which recesses 140 are formed; those recesses communicate to the interior of the shell. A stationary vacuum barrier 143 cooperates with inner surfaces of the die shell over a desired major portion of the circumference of the shell but not over a selected arc 144 of the shell which is partially overlaid by the adjacent upper part of the wedge of heater 141. Arc 144 is substantially within the part of the surface of die 139 with which film 137 has contact. As the die shell rotates around the vacuum barrier, only those recesses subtended by arc 144 are exposed to the vacuum in the die. That vacuum acts upon those exposed die recesses to evacuate them, thereby to draw the portions of film 137 over those recesses into the recesses to form cups or depression in film 137. Film 137 is not subject to vacuum in the die as it reaches the lower portion of the heater wedge and approaches die nip 145.

Preforms 146 are fed to and into the vacuum-formed depressions in film 137, one to each depression, by a suitable preform feeder 147 as the depressions are formed in the film and before they pass under heater 141; the heater thereafter holds the preforms in the recesses of die 139 after the vacuum is released by barrier 143 from the adjacent film areas and until the preforms move into contact with film 136 near die nip 145. As each preform is moved into contact between both of films 136 and 137, it is enrobed by the films by coaction of the dies in the manner described above. A perforated film web 148 emerges from between dies 138 and 139.

In machinery arrangements 120 and 135, the preforms can be handled, if desired, so that they have predetermined positions relative to the dies as they are enrobed by the films so that the seam lines between the film layers applied to the preforms have controlled positions on the preforms.

Machinery arrangements 120 and 135 use dispensation of product preforms in a clocked manner (i.e., in a manner in which each dispensation event is actively timed to the position of a selected component of the machinery via a mechanical linkage between that component and the preform feeding and dispensing mechanism) to one of the moving films at a location substantially spaced from the location where the preforms are enrobed between the films. Clocked feeding of preforms into simultaneous contact with the two films adjacent the place of enrobing die coaction can also be used in the practice of this invention if desired, such as by an arrangement 150 of the kind shown in FIG. 26. Upon comparison of FIGS. 19 and 26, the similarities of machinery arrangement 150 to the presently preferred arrangement described above will be apparent, as will the differences between them.

As shown in FIG. 26, a pair of films 151 and 152 of suitable thickness, composition and condition move along respective film paths which converge at a nip 153 between coacting rotary dies 154 and 155. The dies have working surfaces which are contoured to define plural recesses 156 sized, shaped and spaced in the dies to cooperate with round medicine tablets 31 of the configuration shown in FIGS. 7 and 9, essentially as described above. Tablets 31 are fed, one at a time for each row of recesses in the two dies, into simultaneous contact with films 151 and 152 overlying corresponding pairs of die recesses through a passage 157, which can be vertically disposed, in a core feeder 158. Feeder 158 generally resembles feeder 40 described above in that it has a wedge-shaped heated lower portion 159 positioned symmetrically between dies 154 and 155 above die nip 153. The tablets to be dispensed are stacked in passage 157, preferably all with their major planes of symmetry in a desired plane relative to the die nip line, and the stack extends above a core drive device 160.

Core drive device 160 can be comprised of an eccentric cam 162 mounted on a drive shaft 163 which is so positioned adjacent passage 157 in combination with the cam contour that the cam extends into passage 157 through an opening 164 in the passage roll to contact a tablet in the passage. The cam contour is defined in combination with the rate of rotation of shaft 163 to engage a tablet in the passage each time a pair of recesses 156 reach desired positions at the lower end of the passage and to drive the tablet stack below the engaged tablet a desired distance downwardly in the passage. That distance is defined to be sufficient to move the lowermost tablet in the passage out of the passage enough to be simultaneously contacted by the films adequately to cause the films to securely grab that tablet and carry it with them with the dies and to be enrobed by and sealed between the films in the manner described above. The mechanism (not shown) for rotating shaft 163 is interrelated in a desired manner to the mechanisms for moving the films along their paths. Thus, the feeding of tablets 31 to films 151 and 152 is actively clocked rather than passively self-timed. A resilient element 166 can be carried in a wall of passage 157 very close to the passage open lower end to hold in the passage the tablet just above the one ejected from the passage by operation of cam 162. On the next operation of the cam, the tablet held by the resilient element is driven past the element and out of the passage.

A core feeding arrangement of the kind shown in FIG. 26 can be used to advantage in the practice of this invention where factors such as the size, shape, mass, and number of product cores in passage 157, in combination with other factors such as film thickness, film composition, film elasticity, film surface tack, die velocity, die recess configuration, and die recess spacing, among other factors, do not interrelate sufficiently well to enable the self-timed preform feeding effect described above to be used. For example, such an arrangement can be used where the product preforms are small light tablets.

Soft elastic gelatin capsules, filled with flowable material, are now made by use of rotary die machines similar in many ways to the rotary die machines described above, and also by reciprocating die machines. The principles of this invention can be used with reciprocating die machines having suitable mechanisms for feeding and loading product preforms, such as medicine tablets, into proper contact with the films handled by those machines at suitable places on one of the films.

In addition to gelatin-based films, the films used to define the coating layers applied to product preforms to produce applied-layer enrobed products according to this invention can be prepared from compositions which do not include gelatin. In principle and in fact, the films used in the manufacture of products according to this invention can be films of any composition desired so long as the films, due to their composition, either inherently are or can be treated or conditioned to be plastic (i.e , deformable on a local basis) and sealable (bondable) to another film of the same or different composition without the use of applied adhesives to create the sealing bond between the one and the other films. The films may or may not be elastic and may or may not be of such nature to adhere to things around which they are applied. The presently preferred product of this invention, as noted above, is a medicine tablet to which the applied-film enrobing coating conforms in an airtight manner and to which that coating tightly adheres upon curing (drying) to a hard glass-like state. However, in the case of other applications of the technology provided by this invention, the applied-layer coating may not conform precisely to the thing enrobed, so that the coating generally conforms to the contour of the thing coated, and the coating may not be bonded or adhered to the thing coated. Other films which have been shown to be useful in this broader context include films defined principally by polyvinyl alcohol. Other films which are believed to be useful include films made from starches, modified starches, alginates, modified gelatin, acrylates, polyvinyl pyrrolidone, cellulose derivatives both esters and ethers, and polysiloxanes, among others.

The things produced by use of this invention constitute a new class of packaged product which are materially and discernibly different from gelatin dipped tablets and from other product packages using one or more films, namely, product packages using blister packaging technology or shinkwrap packaging technology. Blister packaging technology involves forming one or more cups in a sheet of material (usually a sheet of thermoplastic synthetic hydrocarbon resin material), dispensing one or more things into the cups, sealing the cups by applying a second sheet over the first sheet and adhering the sheets together, and perhaps cutting or partially perforating the sheets for separation then or later of the sealed cups from each other; such packages are characterized by an appreciable flange in the plane of and around each cup mouth formed by the adhered sheets. Hard gelatin medicine capsules are often individually contained in blister package units. In a common form of shrinkwrap packaging, one or more articles are packaged by placing them centrally on the front face of a card, such as a cardboard card, covering the card front face with a see-through film over the articles and adhering the film to the face of the card around the article or articles, and subjecting the film to a selected agent, such as heat, which causes the film to shrink about the article(s). Products so packaged are often displayed for sale on hooks or rods, rather substantial width of film-covered card extending in all directions in a common plane from the packaged articles(s).

In a product according to this invention, by contrast to blister packaged and shrinkwrap packaged products, the applied-film coating around the thing coated is a package which has essentially no flange extending away from the coated thing. Also, the packaging coating can be part of the product itself, as in the instance of the presently preferred gelatin coated caplet 10 described above, instead of a package to be discarded when the product is used. While a pair of films are applied from opposite directions to an article and those films are sealed in face-abutting relation to each other circumferentially of the article, such events are intermediate events, not final events, in making of a product of this invention; after those intermediate events occur, they are followed by cutting the face-sealed films sufficiently close to the covered article that, in the finished package, the applied films are effectively sealed together in edge-to-edge manner. It will be seen, therefore, that this invention provides a new kind of applied-film product package which is materially different from previously known product packages, including gelatin-dipped medicine tablets.

Workers skilled in the art to which this invention pertains will appreciate that the foregoing descriptions of presently preferred and other embodiments of various aspects of this invention are primarily illustrative and exemplary and are not an exhaustive catalog of all of the ways in which the invention can be embodied. Such workers will appreciate the modifications, variations and alterations can be made to the products, formulations, procedures, and apparatus which has been described without departing from the scope of this invention. Therefore, the following claims defining the patented aspects of this invention are to be read and interpreted in that light consistent with the advances made by this invention over the relevant things previously known.

What is claimed is:

1. A method of film enrobing article preforms such as medicine tablets comprising the steps of
   (A) providing a pair of films of selected thickness and composition each defined to be elastic, plastic and self-adhering to the other film, the films each having obverse and reverse surfaces,
   (B) moving the films along selected paths including through a place of coaction of a pair of coacting dies where the film obverse surfaces contact each other, the dies having cooperating working surfaces contoured for formation between them upon coaction of the dies of at least one cavity sized and shaped for loosely receiving therein a single article preform,
   (C) substantially at the place of die coaction individually dispensing for each cavity formed between the dies an article preform into contact with the obverse surface of at least one of the films at each location on the at least one film which corresponds to the location of a cavity for movement of the dispensed preforms through the place of die coaction,
   (D) at the place of die coaction, stretching the films into contact with each other peripherally around the preforms to cause each preform to be enrobed by and between the films, and sealing the films to each other at lines peripherally around and contiguous to each preform, and
   (E) separating the enrobed preforms from the films essentially at said peripheral lines to provide the articles of manufacture each of which comprises a single preform sealed between applied layers of the film material.

2. The method according to claim 1 including forming the films from a material comprising gelatin in the range of 32 to 50% by weight, a plasticizer in the range of 17 to 35% by weight, and the balance water and colorants.

3. The method according to claim 1 including forming the films from a material comprising gelatin in the range of 40 to 60% by weight, a plasticizer in the range of from 5% to 12% by weight, colorants and pigments not in excess of 3% by weight, and water.

4. The method according to claim 3 including forming the films from a material comprising about 45% gelatin and about 9% plasticizer.

5. The method according to claim 1 including providing the films of gelatin-base material.

6. The method according to claim 5 including providing the films at a thickness in the range of from 0.005 to 0.04 inches.

7. The method according to claim 6 including providing the films at a thickness in the range of from 0.01 to 0.02 inches.

8. The method according to claim 5 including coloring one film differently from the other film.

9. The method according to claim 5 including, at a location proximate the place of die coaction, heating the obverse surface of at least one of the films to a temperature in the range of from 100° F. to 190° F.

10. The method according to claim 5 wherein the article preforms are unitary hard medicine tablets containing at least one active ingredient and which have a plane of symmetry, and including dispensing the tablets in such manner that, upon enrobement of the tablets by the films between the dies, there is formed about each tablet a film seam line which is substantially coincident with the tablet plane of symmetry.

11. The method according to claim 10 wherein the tablets are round.

12. The method according to claim 10 wherein the tablets are caplets and the plane of symmetry is parallel to the length of the caplets.

13. The method according to claim 12 including dispensing the caplets with their lengths aligned with the path of movement of the film to which the caplets are dispensed.

14. The method according to claim 1 including providing the dies as rotary dies rotatable about horizontal axes, and dispensing the preforms into contact with the films from above the place of die coaction along a substantially vertical line.

15. The method according to claim 14 including defining the cavities substantially equally between the dies so that, for each cavity formed between coacting dies, substantially one half said volume is within one die and substantially one half said volume is within the other die, and forming the dies with a plurality of the half-cavity volumes in each die working surface aligned along a line circumferentially of the die and with each half volume spaced a selected small distance from each adjacent one thereof along the line about the die.

16. The method according to claim 15 including disposing a selected plurality of preforms in a column thereof along the vertical line along with the preforms are free to move downwardly by gravity, and allowing the preforms to move freely along the line for movement of the lowermost preform in the column into contact with the films and for movement with the films.

17. The method according to claim 16 including imposing on the films at the place of coaction between the dies a selected amount of tension in each film in the direction of each film path.

18. The method according to claim 14 including performing the dispensing procedure in an internally clocked manner without actively timing movement of the preforms along the vertical with reference to die angular position.

19. A method of film enrobing article preforms such as medicine tablets as articles of manufacture, comprising the steps of
   (A) providing a pair of gelatin-base films of selected thickness and formulation which are elastic, plastic and self-adhering to the other film when at a predetermining temperature within a selected range of temperatures, the films each having obverse and reverse surfaces,
   (B) moving the films at essentially equal velocities along selected paths around and between a pair of matching coacting cylindrical rotary dies between which the film obverse surfaces are adjacent each other, the dies being essentially identical and each defining along at least one line circumferentially of the die a plurality of closely and uniformly spaced cavities in a surface thereof cooperable with the other die,
   (C) stretching the film over the die surfaces at and proximate a place of substantial coaction of the dies with each other,
   (D) at a location along the film paths proximate the place of die coaction, heating the obverse surface of the films to the predetermined temperature, (E) individually dispensing a complete article preform essentially at the place of die coaction into contact with the obverse surfaces of the stretched films at locations on the films which overlie corresponding ones of the die cavities for deformation of the films into the cavities around the preform and for transporting engagement of the preform by the films, (F) at the place of die coaction, forcefully contacting the films with each other peripherally around the preforms to cause each preform to be enrobed by and between the films, and sealing the films to each other peripherally around each preform, and (G) separating the enrobed preforms for the films to provide the articles of manufacture each of which comprises a single preform sealed within a coating of substantially uniform thickness comprised of two gelatin layers sealed together in substantially edge to edge relation.

20. The method according to claim 19 including supplying preforms to the films as a column of preforms of selected height in a vertical passage opening substantially to the place of die coaction at a location between corresponding lines of die cavities, each preform in the passage being free to move along the passage under the bias of gravity and the weight of other preforms above it in the column, and selecting the film thickness, formulation, temperature, and tension and the preform column height in coordination with each other so that preforms self-dispense from the passage to simultaneous contact with the films in synchronism with movement of corresponding opposite die cavities into alignment with each other in response to rotation of the dies.

21. The method according to claim 20 wherein the preforms are essentially identical and each of the preforms has associated with it a selected reference plane, and including supplying each preform to the films with the preform reference plane disposed in a selected orientation relative to the films.

22. The method according to claim 21 including acting upon the preforms in the passage to place each preform in the selected orientation.

23. A method of film enrobing article preforms, such as medicine tablets and the like, as articles or manufacture, comprising the steps of:

drawing together under axial tension, and into surface-to-surface contact at a nip location, a pair of preformed films which are elastic, plastic and capable of adhering to each other, engaging at least one of the films with an article preform at a location on the film which is closely adjacent the nip between the films and at which the at least one film is free to deform laterally around the preform in response to such engagement so that the preform is taken up and drawn by the converging films to the nip, stretching the converging films at the nip around the preform and into contact with each along a line around the preform and substantially contiguous to it to enrobe the preform between the films, sealing the films together along the line, and essentially along the line, whereby there results a flangeless article of manufacture comprised of the preform which is enrobed in a coating of the film material.

24. A process for enrobing an article preform such as a medicine tablet with a substantially solidified biocompatible polymer, the processing comprising the steps of:

drawing together at least two sheets of a substantially solidified biocompatible polymer to form a nip between the converging sheets, dispensing a complete article preform into the nip of the converging sheets, and sealing the sheets of converging polymer about the dispensed preform to enrobe the preform at least partially in the sheets.

25. The process according to claim 24 including providing the biocompatible polymer sheets to have the properties of being elastic, plastic and adherable to each other.

26. The process according to claim 25 wherein the providing step of the process includes casting the sheet from a liquid mixture of gelatin, a plasticizer for gelatin, and water.

27. The process according to claim 26 including performing the casting and drawing steps continuously and concurrently.

28. The process according to claim 26 including formulating the mixture to have a gelatin-to-plasticizer weight ratio in the range of from about 3:1 to about 15:1.

29. The process according to claim 24 including further solidifying the polymer on the preform after performance of the sealing step.

30. The process according to claim 24 including sealing the sheets so that the sheets as sealed fully enrobe the preform and are sealed to each other at all locations along a line encircling the preform and lying contiguous to the preform, and separating the enrobed preform from the sheets essentially along such line.

31. A process for enrobing an article preform such as a medicine tablet with a substantially solidified polymer, the process comprising the steps of:

drawing together at least two sheets of a substantially solidified polymer to form a nip between the converging sheets, dispensing a complete article preform into the nip of the converging sheets, sealing together the converging polymer sheets about the dispensing preform essentially along a line about and closely contiguous to the preform to enrobe the preform at least partially in the polymer, and separating the enrobed preform essentially along said line from the sheets.

32. The process according to claim 31 wherein performance of the sealing step includes conforming the sheets to the preform at substantially all locations on the surface of the preform.

33. The process according to claim 32 wherein performance of the sealing step includes sealing the sheets to each other at all locations along the line.

34. The process according to claim 33 wherein performance of the sealing step includes adhering the polymer to the preform at essentially all points on the surface of the preform.

35. The process according to claim 34 wherein the preform is a medicine tablet having at least one plane of symmetry, and including performing the sealing step to cause the seal line to lie essentially in one of those planes.

36. The process according to claim 34 wherein the preform is a medicine tablet which has an axis of symmetry, and including performing the sealing step to cause the seal line to lie essentially in a plane which includes the tablet axis of symmetry.

37. The process according to claim 31 wherein performance of the drawing step includes disposing the sheets under tension across cooperating die cavities which mate at the nip, and the sealing step includes deforming the tensioned sheets around the dispensed preform from opposite sides thereof at the nip.

38. The process according to claim 31 including providing the sheets of a gelatin-based material comprising gelatin in the range of from about 40 percent to about 60 percent by weight, a plasticizer in the range of from about 5 percent to about 12 percent by weight, the balance comprising water and such pigments and colorants as may be desired.

39. The process according to claim 31 including providing the sheets of a gelatin-based material comprising gelatin and a plasticizer in which the gelatin-to-plasticizer weight ratio is in the range from about 3:1 to about 15:1.

40. The process according to claim 31 wherein performance of the dispensing step includes moving a preform into contact with at least one of the sheets and allowing the contacted preform to be grabbed by the sheet for movement into sheet deforming cooperation with the sheet.

41. The process according to claim 40 wherein the preform moving step includes placing a stack of complete article preforms in contact at a lower end of the stack with the at least one of the converging sheets adjacent to the nip so that the bottom preform in the stack is grabbed and drawn into the nip by at least one sheet.

42. The process according to claim 41 including placing the stack so that the bottom preform in the stack contacts both of the converging sheets.

43. A process for enrobing an article preform such as a medicine tablet with a substantially solidified polymer, the process comprising the steps of:
   drawing together at least two sheets of a substantially solidified polymer to form a nip between the converging sheets,
   placing a stack of complete article preforms in contact at one end with at least one of the converging sheets adjacent to the nip so that the end preform of the stack in contact with a sheet is grabbed and drawn into the nip by at least one of the converging sheets, and
   sealing the two converging polymer sheets about the grabbed and drawn preform to enrobe the preform at least partially in the sheets.

44. The process according to claim 43 wherein there are two sheets of substantially solidified polymer, each of which is elastic, plastic and adherable to the other sheet, and wherein the drawing step includes creating a selected amount of tension in each sheet and disposing the tensioned sheets in surface-to-surface contact with respective dies which are moveable together at the nip to place the sheets in surface-to-surface contact and which cooperate at the nip to form a cavity sized and configured to loosely accommodate the preform therein, and including placing the stack of preforms so that the end preform contacts the two tensioned converging sheets essentially simultaneously.

45. The process according to claim 44 including coordinating the drawing, sheet tensioning and preform stack placing operations so that the sheets grab the stack end preform at locations on the sheets which cause the grabbed preform to be placed between the sheets within the cavity.

46. The process according to claim 45 including performing the sealing operation to seal the sheets about the preform essentially along a line about and closely contiguous to the perform, and including separating the enrobed preform from the sheets essentially along that line.

47. The process according to claim 45 wherein the dies are configured for forming at the nip at different times respective one of a plurality of cavities each sized and configured to loosely accommodate a preform therein, and including forming the stack of preforms so that as the stack end preform is grabbed and drawn into the nip, the next preform in the stack moves to become the stack end preform.

48. The process according to claim 43 including forming the stack of preforms for self-metering of the stack end preform into contact with the at least one sheet.

49. The process according to claim 43 including forcing the stack end preform into contact with the at least one sheet.

50. The process according to claim 43 performance of the sealing step includes conforming and adhering the sheets to the grabbed preform.

51. The process according to claim 50 wherein the preform is a medicine tablet and the polymer is gelatin, and including sealing the sheets together at all locations along a line about and closely contiguous to the preform.

52. The process according to claim 51 wherein the tablet has a plane of symmetry, and including creating the stack of tablet preforms so that at least the stack end tablet has its plane of symmetry disposed essentially parallel to the nip, and sealing the sheets so that the seal line lies substantially in the tablet plane of symmetry.

53. The process according to claim 51 wherein the tablet has an axis of symmetry, and including creating the stack of tablet preforms so that at least the stack end tablet has its axis of symmetry disposed normal to the nip, and sealing the sheets so that the seal line lies in a plane which includes the tablet axis of symmetry.

54. The process according to claim 43 wherein the preform is a medicine tablet and the polymer is gelatin, and including forming the sheets form a mixture of gelatin and a plasticizer so that the formed sheets have a gelatin-to-plasticizer weight ratio in the range of from about 3:1 to about 15:1.

* * * * *

UNITED STATES PATENT AND TRADEMARK OFFICE
CERTIFICATE OF CORRECTION

PATENT NO. : 5,146,730
DATED : September 15, 1992
INVENTOR(S) : Hani Sadek; Gregory L. Dietel It is certified that error appears in the above-identified patent and that said Letters Patent is hereby corrected as shown below:

Column 30, lines 50,51, change "predetermining" to
-- predetermined --.

Column 31, line 14, after "preforms" change "for" to
-- from --.

Column 31, line 44, after "articles" change "or" to
-- of --.

Column 31, line 61, after "line, and" insert
-- separating the enrobed preform from
the films --.

Signed and Sealed this

Second Day of November, 1993

Attest:

BRUCE LEHMAN

Attesting Officer     Commissioner of Patents and Trademarks